(12) United States Patent
Iimori et al.

(10) Patent No.: US 9,822,148 B2
(45) Date of Patent: Nov. 21, 2017

(54) EGFR-BINDING PEPTIDE

(71) Applicant: HOYA CORPORATION, Tokyo (JP)

(72) Inventors: Yusuke Iimori, Tokyo (JP); Mizue Yamagata, Tokyo (JP); Toshitaka Shiono, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 82 days.

(21) Appl. No.: 14/410,329

(22) PCT Filed: Jun. 18, 2013

(86) PCT No.: PCT/JP2013/066762
§ 371 (c)(1),
(2) Date: Dec. 22, 2014

(87) PCT Pub. No.: WO2014/002836
PCT Pub. Date: Jan. 3, 2014

(65) Prior Publication Data
US 2015/0337012 A1   Nov. 26, 2015

(30) Foreign Application Priority Data

Jun. 25, 2012 (JP) ................. 2012-141700

(51) Int. Cl.
| | | |
|---|---|---|
| C07K 7/08 | (2006.01) | |
| G01N 33/574 | (2006.01) | |
| A61K 38/00 | (2006.01) | |
| C07K 14/47 | (2006.01) | |

(52) U.S. Cl.
CPC ............. *C07K 7/08* (2013.01); *A61K 38/00* (2013.01); *C07K 14/4702* (2013.01); *G01N 33/574* (2013.01); *G01N 33/57492* (2013.01); *G01N 2333/71* (2013.01)

(58) Field of Classification Search
None
See application file for complete search history.

(56) References Cited

U.S. PATENT DOCUMENTS

| | | |
|---|---|---|
| 7,598,350 B2 | 10/2009 | Liu et al. |
| 2010/0151003 A1 | 6/2010 | Trikha et al. |
| 2010/0278851 A1 | 11/2010 | Itoh et al. |
| 2011/0144065 A1 | 6/2011 | Denardo et al. |
| 2012/0021006 A1 | 1/2012 | Levitzki et al. |
| 2012/0330998 A1 | 12/2012 | Yacov et al. |
| 2015/0343041 A1 | 12/2015 | Itoh et al. |

FOREIGN PATENT DOCUMENTS

| | | |
|---|---|---|
| CN | 102325794 | 1/2012 |
| JP | 2008-501308 | 1/2008 |
| JP | 2010-154842 | 7/2010 |
| JP | 4734319 | 7/2011 |
| JP | 4808412 | 11/2011 |
| WO | 96/40210 | 12/1996 |
| WO | 98/24893 | 6/1998 |
| WO | 2005/081854 | 9/2005 |
| WO | 2008/079973 | 7/2008 |
| WO | 2009/038026 | 3/2009 |
| WO | 2009/132020 | 10/2009 |
| WO | 2010/064207 | 6/2010 |

OTHER PUBLICATIONS

Li et al., "Identification and characterization of a novel peptide ligand of epidermal growth factor receptor for targeted delivery of therapeutics," *The FASEB Journal*, vol. 19, No. 14, pp. 1978-1985, 2005.
Riemer et al., "Vaccination With Cetuximab Mimotopes and Biological Properties of Induced Anti-Epidermal Growth Factor Receptor Antibodies," *Journal of the National Cancer Institute*, vol. 97, No. 22, pp. 1663-1670, 2005.
Jeong et al., "In vivo and in vitro evaluation of Cy5.5 conjugated epidermal growth factor receptor binding peptide," *Nuclear Medicine and Biology*, vol. 39, No. 6, pp. 805-812, 2012.
Hamzeh-Mivehroud et al., "Identification of New Peptide Ligands for Epidermal Growth Factor Receptor Using Phage Display and Computationally Modeling their Mode of Binding," *Chemical Biology and Drug Design*, vol. 79, No. 3, pp. 246-259, 2012.
Abourbeh et al., "PolyIC GE11 Polyplex Inhibits EGFR-Overexpressing Tumors," *IUBMB Life*, vol. 64, No. 4, pp. 324-330, 2012.
International Search Report for PCT/JP2013/066762, dated Sep. 10, 2013.
International Preliminary Report on Patentability for PCT/JP2013/066762, dated Jan. 8, 2015.

(Continued)

*Primary Examiner* — James H Alstrum Acevedo
*Assistant Examiner* — Tara Martinez
(74) *Attorney, Agent, or Firm* — Greenblum & Bernstein, P.L.C.

(57) ABSTRACT

Provided are a substance capable of binding to EGFR specifically with a high affinity and a pharmaceutical agent containing the substance. A peptide which contains at least an amino acid sequence is represented by the formula (1), (2) or (3), as described in the specification, and is composed of 12 to 50 amino acids:

(SEQ ID NO: 55)
$X^1$-His-$X^2$-$X^3$-Asp-$X^4$-$X^5$-$X^6$-$X^7$-$X^8$-Trp-His (1)

(SEQ ID NO: 56)
Phe-His-Asp-Trp-$X^{11}$-Pro-$X^{12}$-$X^{13}$-$X^{14}$-$X^{15}$-$X^{16}$-$X^{17}$ (2)

(SEQ ID NO: 57)
Leu-His-$X^{21}$-Ser-$X^{22}$-Trp-Met-$X^{23}$-$X^{24}$-$X^{25}$-$X^{26}$-$X^{27}$ (3).

10 Claims, 21 Drawing Sheets

(56) References Cited

OTHER PUBLICATIONS

Chinese Office Action issued in CN Patent Appl. No. 201380031904.4, dated Feb. 3, 2016, along with an English language translation.
Ongarora et al., "Phthalocyanine-Peptide Conjugates for Epidermal Growth Factor Receptor Targeting", *J. Med. Chem.*, vol. 55, No. 8, pp. 3725-3738, 2012.
Song et al., "Novel Peptide Ligand Directs Liposomes Toward EGF-R High-Expressing Cancer Cells in Vitro and in Vivo", *The FASEB Journal*, vol. 23, No. 5, pp. 1396-1404, 2009.
Lv et al., "EGFR-Binding Peptide: a Patent Evaluation of WO2014002836", *Expert. Opin. Ther. Pat.*, vol. 24, No. 12, pp. 1409-1411, 2014.
Partial Supplementary European Search Report issued in EP Patent Application No. 13809117.8, dated Nov. 23, 2015.
Japanese Office Action issued in JP Patent Appl. No. 2012-141700, dated Mar. 22, 2016, along with an English language translation.

Figure 3

| | | |
|---|---|---|
| I-1010 | W H L S D L W Q N A W H | (Seq. ID No. 2) |
| I-1011 | T A M P V W A M E R H R | (Seq. ID No. 3) |
| I-1012 | F H D W L P E V S P P D | (Seq. ID No. 4) |
| I-1013 | Q V T S I Y H M Y M L N | (Seq. ID No. 5) |
| I-1014 | K P T Y M D L I P G S L | (Seq. ID No. 6) |
| I-1015 | L H Q S E W M Y V D I H | (Seq. ID No. 7) |
| I-1016 | F H R W S P E I D T E M | (Seq. ID No. 8) |
| I-1017 | L V S T H A A T V L L S | (Seq. ID No. 9) |

Figure 9

| | | |
|---|---|---|
| I-1010_W1A | A H L S D L W Q N A W H | (Seq. ID No. 11) |
| I-1010_H2A | W A L S D L W Q N A W H | (Seq. ID No. 12) |
| I-1010_L3A | W H A S D L W Q N A W H | (Seq. ID No. 13) |
| I-1010_S4A | W H L A D L W Q N A W H | (Seq. ID No. 14) |
| I-1010_D5A | W H L S A L W Q N A W H | (Seq. ID No. 15) |
| I-1010_L6A | W H L S D A W Q N A W H | (Seq. ID No. 16) |
| I-1010_W7A | W H L S D L A Q N A W H | (Seq. ID No. 17) |
| I-1010_Q8A | W H L S D L W A N A W H | (Seq. ID No. 18) |
| I-1010_N9A | W H L S D L W Q A A W H | (Seq. ID No. 19) |
| I-1010_W11A | W H L S D L W Q N A A H | (Seq. ID No. 20) |
| I-1010_H12A | W H L S D L W Q N A W A | (Seq. ID No. 21) |

Figure 10

| | | |
|---|---|---|
| I-1012_F1A | A H D W L P E V S P P D | (Seq. ID No. 22) |
| I-1012_H2A | F A D W L P E V S P P D | (Seq. ID No. 23) |
| I-1012_D3A | F H A W L P E V S P P D | (Seq. ID No. 24) |
| I-1012_W4A | F H D A L P E V S P P D | (Seq. ID No. 25) |
| I-1012_L5A | F H D W A P E V S P P D | (Seq. ID No. 26) |
| I-1012_P6A | F H D W L A E V S P P D | (Seq. ID No. 27) |
| I-1012_E7A | F H D W L P A V S P P D | (Seq. ID No. 28) |
| I-1012_V8A | F H D W L P E A S P P D | (Seq. ID No. 29) |
| I-1012_S9A | F H D W L P E V A P P D | (Seq. ID No. 30) |
| I-1012_P10A | F H D W L P E V S A P D | (Seq. ID No. 31) |
| I-1012_P11A | F H D W L P E V S P A D | (Seq. ID No. 32) |
| I-1012_D12A | F H D W L P E V S P P A | (Seq. ID No. 33) |

Figure 11

| | | |
|---|---|---|
| I-1015_L1A | A H Q S E W M Y V D I H | (Seq. ID No. 34) |
| I-1015_H2A | L A Q S E W M Y V D I H | (Seq. ID No. 35) |
| I-1015_Q3A | L H A S E W M Y V D I H | (Seq. ID No. 36) |
| I-1015_S4A | L H Q A E W M Y V D I H | (Seq. ID No. 37) |
| I-1015_E5A | L H Q S A W M Y V D I H | (Seq. ID No. 38) |
| I-1015_W6A | L H Q S E A M Y V D I H | (Seq. ID No. 39) |
| I-1015_M7A | L H Q S E W A Y V D I H | (Seq. ID No. 40) |
| I-1015_Y8A | L H Q S E W M A V D I H | (Seq. ID No. 41) |
| I-1015_V9A | L H Q S E W M Y A D I H | (Seq. ID No. 42) |
| I-1015_D10A | L H Q S E W M Y V A I H | (Seq. ID No. 43) |
| I-1015_I11A | L H Q S E W M Y V D A H | (Seq. ID No. 44) |
| I-1015_H12A | L H Q S E W M Y V D I A | (Seq. ID No. 45) |

Figure 15

| | | |
|---|---|---|
| I-1010_W1F | F H L S D L W Q N A W H | (Seq. ID No. 46) |
| I-1010_L3M | W H M S D L W Q N A W H | (Seq. ID No. 47) |
| I-1010_L3I | W H I S D L W Q N A W H | (Seq. ID No. 48) |
| I-1010_L3V | W H V S D L W Q N A W H | (Seq. ID No. 49) |
| I-1010_W7F | W H L S D L F Q N A W H | (Seq. ID No. 50) |
| I-1010_W7Y | W H L S D L Y Q N A W H | (Seq. ID No. 51) |
| I-1010_W1F/Q8A | F H L S D L W A N A W H | (Seq. ID No. 52) |
| I-1010_L3M/Q8A | W H M S D L W A N A W H | (Seq. ID No. 53) |

SEQUENCE LISTING

```
<160> NUMBER OF SEQ ID NOS: 57

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Designed primer based on M13KE phage

<400> SEQUENCE: 1
ccctcatagt tagcgtaacg                                                  20

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1010
```

```
<400> SEQUENCE: 2

Trp His Leu Ser Asp Leu Trp Gln Asn Ala Trp His
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1011

<400> SEQUENCE: 3

Thr Ala Met Pro Val Trp Ala Met Glu Arg His Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1012

<400> SEQUENCE: 4

Phe His Asp Trp Leu Pro Glu Val Ser Pro Pro Asp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1013

<400> SEQUENCE: 5

Gln Val Thr Ser Ile Tyr His Met Tyr Met Leu Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1014

<400> SEQUENCE: 6

Lys Pro Thr Tyr Met Asp Leu Ile Pro Gly Ser Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: I-1015

<400> SEQUENCE: 7

Leu His Gln Ser Glu Trp Met Tyr Val Asp Ile His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1016

<400> SEQUENCE: 8

Phe His Arg Trp Ser Pro Glu Ile Asp Thr Glu Met
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I-1017

<400> SEQUENCE: 9

Leu Val Ser Thr His Ala Ala Thr Val Leu Leu Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Random peptide

<400> SEQUENCE: 10

Gly Ala Ala Ser Arg Thr Tyr Leu His Glu Leu Ile
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W1A)

<400> SEQUENCE: 11

Ala His Leu Ser Asp Leu Trp Gln Asn Ala Trp His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Designed peptide based on I-1010(H2A)

<400> SEQUENCE: 12

Trp Ala Leu Ser Asp Leu Trp Gln Asn Ala Trp His
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L3A)

<400> SEQUENCE: 13

Trp His Ala Ser Asp Leu Trp Gln Asn Ala Trp His
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(S4A)

<400> SEQUENCE: 14

Trp His Leu Ala Asp Leu Trp Gln Asn Ala Trp His
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(D5A)

<400> SEQUENCE: 15

Trp His Leu Ser Ala Leu Trp Gln Asn Ala Trp His
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L6A)

<400> SEQUENCE: 16

Trp His Leu Ser Asp Ala Trp Gln Asn Ala Trp His
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: Designed peptide based on I-1010(W7A)

<400> SEQUENCE: 17

Trp His Leu Ser Asp Leu Ala Gln Asn Ala Trp His
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(Q8A)

<400> SEQUENCE: 18

Trp His Leu Ser Asp Leu Trp Ala Asn Ala Trp His
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(N9A)

<400> SEQUENCE: 19

Trp His Leu Ser Asp Leu Trp Gln Ala Ala Trp His
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W11A)

<400> SEQUENCE: 20

Trp His Leu Ser Asp Leu Trp Gln Asn Ala Ala His
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(H12A)

<400> SEQUENCE: 21

Trp His Leu Ser Asp Leu Trp Gln Asn Ala Trp Ala
1               5                   10

<210> SEQ ID NO 22
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: Designed peptide based on I-1012(F1A)

<400> SEQUENCE: 22

Ala His Asp Trp Leu Pro Glu Val Ser Pro Pro Asp
1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(H2A)

<400> SEQUENCE: 23

Phe Ala Asp Trp Leu Pro Glu Val Ser Pro Pro Asp
1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(D3A)

<400> SEQUENCE: 24

Phe His Ala Trp Leu Pro Glu Val Ser Pro Pro Asp
1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(W4A)

<400> SEQUENCE: 25

Phe His Asp Ala Leu Pro Glu Val Ser Pro Pro Asp
1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(L5A)

<400> SEQUENCE: 26

Phe His Asp Trp Ala Pro Glu Val Ser Pro Pro Asp
1               5                  10

<210> SEQ ID NO 27
<211> LENGTH: 12
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<223> OTHER INFORMATION: Designed peptide based on I-1012(P6A)

<400> SEQUENCE: 27

Phe His Asp Trp Leu Ala Glu Val Ser Pro Pro Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(E7A)

<400> SEQUENCE: 28

Phe His Asp Trp Leu Pro Ala Val Ser Pro Pro Asp
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(V8A)

<400> SEQUENCE: 29

Phe His Asp Trp Leu Pro Glu Ala Ser Pro Pro Asp
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(S9A)

<400> SEQUENCE: 30

Phe His Asp Trp Leu Pro Glu Val Ala Pro Pro Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(P10A)

<400> SEQUENCE: 31

Phe His Asp Trp Leu Pro Glu Val Ser Ala Pro Asp
1               5                   10

<210> SEQ ID NO 32
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-2012(P11A)

<400> SEQUENCE: 32

Phe His Asp Trp Leu Pro Glu Val Ser Pro Ala Asp
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1012(D12A)

<400> SEQUENCE: 33

Phe His Asp Trp Leu Pro Glu Val Ser Pro Pro Ala
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(L1A)

<400> SEQUENCE: 34

Ala His Gln Ser Glu Trp Met Tyr Val Asp Ile His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(H2A)

<400> SEQUENCE: 35

Leu Ala Gln Ser Glu Trp Met Tyr Val Asp Ile His
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(Q3A)

<400> SEQUENCE: 36

Leu His Ala Ser Glu Trp Met Tyr Val Asp Ile His
1               5                   10

<210> SEQ ID NO 37
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(S4A)

<400> SEQUENCE: 37

Leu His Gln Ala Glu Trp Met Tyr Val Asp Ile His
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(E5A)

<400> SEQUENCE: 38

Leu His Gln Ser Ala Trp Met Tyr Val Asp Ile His
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(W6A)

<400> SEQUENCE: 39

Leu His Gln Ser Glu Ala Met Tyr Val Asp Ile His
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(M7A)

<400> SEQUENCE: 40

Leu His Gln Ser Glu Trp Ala Tyr Val Asp Ile His
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(Y8A)

<400> SEQUENCE: 41

Leu His Gln Ser Glu Trp Met Ala Val Asp Ile His
1               5                   10

<210> SEQ ID NO 42
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(V9A)

<400> SEQUENCE: 42

Leu His Gln Ser Glu Trp Met Tyr Ala Asp Ile His
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(D10A)

<400> SEQUENCE: 43

Leu His Gln Ser Glu Trp Met Tyr Val Ala Ile His
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(I11A)

<400> SEQUENCE: 44

Leu His Gln Ser Glu Trp Met Tyr Val Asp Ala His
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1015(H12A)

<400> SEQUENCE: 45

Leu His Gln Ser Glu Trp Met Tyr Val Asp Ile Ala
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W1F)

<400> SEQUENCE: 46

Phe His Leu Ser Asp Leu Trp Gln Asn Ala Trp His
1               5                   10
```

```
<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L3M)

<400> SEQUENCE: 47

Trp His Met Ser Asp Leu Trp Gln Asn Ala Trp His
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L3I)

<400> SEQUENCE: 48

Trp His Ile Ser Asp Leu Trp Gln Asn Ala Trp His
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L3V)

<400> SEQUENCE: 49

Trp His Val Ser Asp Leu Trp Gln Asn Ala Trp His
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W7F)

<400> SEQUENCE: 50

Trp His Leu Ser Asp Leu Phe Gln Asn Ala Trp His
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W7Y)

<400> SEQUENCE: 51

Trp His Leu Ser Asp Leu Tyr Gln Asn Ala Trp His
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(W1F/Q8A)

<400> SEQUENCE: 52

Phe His Leu Ser Asp Leu Trp Ala Asn Ala Trp His
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Designed peptide based on I-1010(L3M/Q8A)

<400> SEQUENCE: 53

Trp His Met Ser Asp Leu Trp Ala Asn Ala Trp His
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Random peptide

<400> SEQUENCE: 54

Tyr Leu Pro Leu Trp Arg Leu Ser Glu Ser His Met
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or Phe
<220> FEATURE:
<221> NAME/KEY: MOD_RES
<222> LOCATION: (3)..(3)
<223> OTHER INFORMATION: Leu, Met, Ile or Val
<220> FEATURE:
<221> NAME/KEY: MOD_RES
<222> LOCATION: (4)..(4)
<223> OTHER INFORMATION: Ser, Ala, Thr, Gly, Asn, Asp, Glu, Arg or Lys
<220> FEATURE:
<221> NAME/KEY: MOD_RES
<222> LOCATION: (6)..(6)
<223> OTHER INFORMATION: Leu, Met, Ile, Val, Ala, Phe, Tyr, Trp, His or
      Cys
<220> FEATURE:
<221> NAME/KEY: MOD_RES
<222> LOCATION: (7)..(7)
<223> OTHER INFORMATION: Trp, Phe or Tyr
<220> FEATURE:
<221> NAME/KEY: MOD_RES

```
<222> LOCATION: (8)..(8)
<223> OTHER INFORMATION: Gln, Asn, Asp, Glu, Ala, Ser, Thr, Leu, Met,
      Lys or Arg
<220> FEATURE:
<221> NAME/KEY: MOD_RES
<222> LOCATION: (9)..(9)
<223> OTHER INFORMATION: Asn, Gln, Asp, Glu, Ser, Thr, Ala, Gly, Lys or
      Arg
<220> FEATURE:
<221> NAME/KEY: MOD_RES
<222> LOCATION: (10)..(10)
<223> OTHER INFORMATION: Ala, Gly, Ser, Thr, Asn, Val or Cys

<400> SEQUENCE: 55

Xaa His Xaa Xaa Asp Xaa Xaa Xaa Xaa Xaa Trp His
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Leu, Met, Ile, Val, Ala, Phe, Tyr, Trp, His or
      Cys
<220> FEATURE:
<221> NAME/KEY: MOD_RES
<222> LOCATION: (7)..(7)
<223> OTHER INFORMATION: Glu, Asp, Gln, Asn, Ala, Ser, Thr, Lys, Arg or
      His
<220> FEATURE:
<221> NAME/KEY: MOD_RES
<222> LOCATION: (8)..(8)
<223> OTHER INFORMATION: Val, Ala, Leu, Ile, Met, Thr, Cys or Asn
<220> FEATURE:
<221> NAME/KEY: MOD_RES
<222> LOCATION: (9)..(9)
<223> OTHER INFORMATION: Ser, Ala, Thr, Gly, Asn, Asp, Glu, Arg or Lys
<220> FEATURE:
<221> NAME/KEY: MOD_RES
<222> LOCATION: (10)..(10)
<223> OTHER INFORMATION: Pro, Val, Ile, Lys, Ala, Met, Trp, Tyr, Ser,
      Thr, Cys or Phe
<220> FEATURE:
<221> NAME/KEY: MOD_RES
<222> LOCATION: (11)..(11)
<223> OTHER INFORMATION: Pro, Val, Ile, Lys, Ala, Met, Trp, Tyr, Ser,
      Thr, Cys or Phe
<220> FEATURE:
<221> NAME/KEY: MOD_RES
<222> LOCATION: (12)..(12)
<223> OTHER INFORMATION: Asp, Glu, Asn, Gln, Ala, Ser, Thr, Lys, Arg or
      His

<400> SEQUENCE: 56

Phe His Asp Trp Xaa Pro Xaa Xaa Xaa Xaa Xaa Xaa
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gln, Asn, Asp, Glu, Ala, Ser, Thr, Leu, Met,
      Lys or Arg
<220> FEATURE:
```

```
<221> NAME/KEY: MOD_RES
<222> LOCATION: (5)..(5)
<223> OTHER INFORMATION: Glu, Asp, Gln, Asn, Ala, Ser, Thr, Lys, Arg or
      His
<220> FEATURE:
<221> NAME/KEY: MOD_RES
<222> LOCATION: (8)..(8)
<223> OTHER INFORMATION: Tyr, Phe, Trp, His, Leu, Met, Ile, Val, Cys or
      Ala
<220> FEATURE:
<221> NAME/KEY: MOD_RES
<222> LOCATION: (9)..(9)
<223> OTHER INFORMATION: Val, Ala, Leu, Ile, Met, Thr, Cys or Asn
<220> FEATURE:
<221> NAME/KEY: MOD_RES
<222> LOCATION: (10)..(10)
<223> OTHER INFORMATION: Asp, Glu, Asn, Gln, Ala, Ser, Thr, Lys, Arg or
      His
<220> FEATURE:
<221> NAME/KEY: MOD_RES
<222> LOCATION: (11)..(11)
<223> OTHER INFORMATION: Ile, Val, Leu, Met, Ala, Phe, Tyr, Trp or Gly
<220> FEATURE:
<221> NAME/KEY: MOD_RES
<222> LOCATION: (12)..(12)
<223> OTHER INFORMATION: His, Tyr, Phe, Lys, Arg, Leu, Met or Ala

<400> SEQUENCE: 57

Leu His Xaa Ser Xaa Trp Met Xaa Xaa Xaa Xaa Xaa
1               5                   10
```

EGFR-BINDING PEPTIDE

SEQUENCE LISTING

The instant application contains a Sequence Listing which has been submitted electronically in ASCII format and is hereby incorporated by reference in its entirety. Said ASCII copy, created on Mar. 22, 2016, is named P46495_SL.txt and is 19,287 bytes in size.

FIELD OF THE INVENTION

The present invention relates to a peptide that specifically binds to an epidermal growth factor receptor (EGFR) and a pharmaceutical agent containing the same.

BACKGROUND OF THE INVENTION

EGFR is a receptor recognizing an epidermal growth factor, that controls cell proliferation and growth and transmitting signals, and plays an important role in cellular functions such as cell proliferation, differentiation and migration. According to signals from the EGFR, cell proliferation is promoted, apoptosis is suppressed, and mobility of tumor cells and new blood vessel growth are increased. EGFR functions in tumor specific manner, and its high expression is observed within a wide range of tumors in human epithelial tissues including non-small-cell lung cancer (NSCLC), breast cancer, squamous cell carcinoma of the head and neck (SCCHN), stomach cancer, colon cancer, esophageal cancer, prostate cancer, urinary bladder cancer, kidney cancer, colon cancer, and ovarian cancer.

According to these discoveries, EGFR is recognized as an important target for a delivery system mediating between a drug and a receptor of a gene in a cancer treatment. However, EGF, that is a ligand of EGFR, remarkably enhances mitotic division and angiogenesis, and it is therefore important to find a substrate such as EGF. A peptide ligand which can be easily diffused and shows low immunogenicity, and also can easily take in a gene transportation vector, has been studied as a target site for selectively delivering radionuclides, cytokines, chemical drugs, and therapeutic genes to a tumor. Recently, a research result of obtaining a peptide ligand by use of phage library screening has been reported (Non-Patent Document 1).

On the other hand, a receptor protein belonging to an EGFR family member is one of the best-characterized targets of cancer cells. The EGF family including EGFR known as HER1 or ErbB1, HER2 known as ErbB2 or neu, HER3 (ErbB3) and HER4 (ErbB4) is important in cell survival, differentiation and proliferation. In particular, when EGFR signal is increased, it associates with carcinogenic transformation. As a result, independent cell survival, tumor invasion, new blood vessel growth and metastasis are induced. Expression of EGFR and high expression thereof have been reported in various tumor types, a high expression level of EGFR in one third of epithelial cancers has been known, and high expression of EGFR is frequently associated with adverse prognosis. Furthermore, EGFR is known to be related to generation and growth of cancer, and drugs for chemotherapy targeting EGFR have been developed. Cetuximab (IMC-C225, Erbitax) which is one of inhibitors of EGFR is a monoclonal antibody approved as a therapeutic agent for metastatic colon cancer by FDA. Cetuximab is a human-mouse chimeric antibody and targets an extracellular domain of EGFR. Cetuximab binds to EGFR with higher affinity than EGF and a TFG-α that are original ligands and competitively inhibits binding to EGFR to suppress the activity (Non-Patent Document 2, Patent Document 1). Another example of a human anti-EGFR monoclonal antibody includes panitumumab (Vectibix (registered trademark)) (Patent Document 2).

CITATION LIST

Patent Documents

Patent Document 1: WO No. 1996/040210
Patent Document 2: Japanese Patent No. 4808412

Non-Patent Documents

Non-Patent Document 1: The FASEB Journal, 2005; 19, 1978-1985
Non-Patent Document 2: Journal of the National Cancer Institute, 2005; 97 (22), 1663-1670

SUMMARY OF THE INVENTION

Problems to be Solved by the Invention

However, an already reported peptide ligand of EGFR has insufficient binding properties to EGFR and an anti-EGFR antibody has a large molecular weight and thus causes problems such as limited administration routes and occurrence of side effects.

Therefore, an object of the present invention is to provide a substance capable of binding to EGFR specifically with a high affinity and a pharmaceutical agent containing the same.

Means for Solving the Problems

Accordingly, the present inventors searched for a phage that displays a peptide specifically binding to EGFR by use of a phage display method, and found that a peptide having a specific amino acid sequence specifically binds to a recombinant human EGFR protein, and cells and tissues, which express EGFR, can be specifically detected by use of this peptide or a labeled product thereof. Furthermore, the present inventors found that the peptide or a labeled product thereof is also useful as a cancer therapeutic agent on the grounds that the peptide or a labeled product thereof competitively inhibits binding between EGFR and EGF, and thus completed the invention.

That is, the present invention is to provide the following [1] to [19].

[1] A peptide, which comprises an amino acid sequence represented by at least the formula (1), (2) or (3) described below and is composed of 12 to 50 amino acids:

$X^1$-His-$X^2$-$X^3$-Asp-$X^4$-$X^5$-$X^6$-$X^7$-$X^8$-Trp-His  (1)(SEQ ID NO: 55)

(wherein $X^1$ represents Trp or Phe;
$X^2$ represents Leu, Met, Ile or Val;
$X^3$ represents Ser, Ala, Thr, Gly, Asn, Asp, Glu, Arg or Lys;
$X^4$ represents Leu, Met, Ile, Val, Ala, Phe, Tyr, Trp, His or Cys;
$X^5$ represents Trp, Phe or Tyr;
$X^6$ represents Gln, Asn, Asp, Glu, Ala, Ser, Thr, Leu, Met, Lys or Arg;

X⁷ represents Asn, Gln, Asp, Glu, Ser, Thr, Ala, Gly, Lys or Arg; and

X⁸ represents Ala, Gly, Ser, Thr, Asn, Val or Cys):

Phe-His-Asp-Trp-X¹¹-Pro-X¹²-X¹³-X¹⁴-X¹⁵-X¹⁶-X¹⁷ (SEQ ID NO: 56)

(wherein X¹¹ represents Leu, Met, Ile, Val, Ala, Phe, Tyr, Trp, His or Cys;

X¹² represents Glu, Asp, Gln, Asn, Ala, Ser, Thr, Lys, Arg or His;

X¹³ represents Val, Ala, Leu, Ile, Met, Thr, Cys or Asn;

X¹⁴ represents Ser, Ala, Thr, Gly, Asn, Asp, Glu, Arg or Lys;

X¹⁵ represents Pro, Val, Ile, Lys, Ala, Met, Trp, Tyr, Ser, Thr, Cys or Phe;

X¹⁶ represents Pro, Val, Ile, Lys, Ala, Met, Trp, Tyr, Ser, Thr, Cys or Phe; and X¹⁷ represents Asp, Glu, Asn, Gln, Ala, Ser, Thr, Lys, Arg or His), and Leu-His-X²¹-Ser-X²²-Trp-Met-X²³-X²⁴-X²⁵-X²⁶-X²⁷ (SEQ ID NO: 57)

(wherein X²¹ represents Gln, Asn, Asp, Glu, Ala, Ser, Thr, Leu, Met, Lys or Arg;

X²² represents Glu, Asp, Gln, Asn, Ala, Ser, Thr, Lys, Arg or His;

X²³ represents Tyr, Phe, Trp, His, Leu, Met, Ile, Val, Cys or Ala;

X²⁴ represents Val, Ala, Leu, Ile, Met, Thr, Cys or Asn;

X²⁵ represents Asp, Glu, Asn, Gln, Ala, Ser, Thr, Lys, Arg or His;

X²⁶ represents Ile, Val, Leu, Met, Ala, Phe, Tyr, Trp or Gly; and

X²⁷ represents His, Tyr, Phe, Lys, Arg, Leu, Met or Ala.)

[2] The peptide according to [1], wherein, in the formula (1), X¹ represents Trp or Phe, X² represents Leu, Met, Ile or Val, X³ represents Ser, Ala, Thr, Gly or Asn, X⁴ represents Leu, Met, Ile, Val or Ala, X⁵ represents Trp or Phe, X⁶ represents Gln, Asn or Ala, X⁷ represents Asn, Gln or Ala, and X⁸ represents Ala, Gly, Ser or Thr.

[3] The peptide according to [1], wherein, in the formula (1), X¹ represents Trp or Phe, X² represents Leu, Met, Ile or Val, X³ represents Ser or Ala, X⁴ represents Leu or Ala, X⁵ represents Trp, X⁶ represents Gln or Ala, X⁷ represents Asn or Ala, and X⁸ represents Ala.

[4] The peptide according to [1], wherein, in the formula (2), X¹¹ represents Leu, Met, Ile, Val or Ala, X¹² represents Glu, Asp, Gln, Asn or Ala, X¹³ represents Val, Ala, Leu or Ile, X¹⁴ represents Ser, Ala, Thr, Gly or Asn, X¹⁵ represents Pro, Val, Ile or Ala, X¹⁶ represents Pro, Val, Ile or Ala, and X¹⁷ represents Asp, Glu, Asn, Gln or Ala.

[5] The peptide according to [1], wherein, in the formula (2), X¹¹ represents Leu or Ala, X¹² represents Glu or Ala, X¹³ represents Val or Ala, X¹⁴ represents Ser or Ala, X¹⁵ represents Pro or Ala, X¹⁶ represents Pro or Ala, and X¹⁷ represents Asp or Ala.

[6] The peptide according to [1], wherein, in the formula (3), X²¹ represents Gln, Asn or Ala, X²² represents Glu, Asp, Gln or Ala, X²³ represents Tyr, Phe, Trp, His or Ala, X²⁴ represents Val, Ala, Leu or Ile, X²⁵ represents Asp, Glu, Asn, Gln or Ala, X²⁶ represents Ile, Val, Leu, Met or Ala, and X²⁷ represents His, Tyr, Phe, Lys, Arg or Ala.

[7] The peptide according to [1], wherein, in the formula (3), X²¹ represents Gln or Ala, X²² represents Glu or Ala, X²³ represents Tyr or Ala, X²⁴ represents Val or Ala, X²⁵ represents Asp or Ala, X²⁶ represents Ile or Ala, and X²⁷ represents His or Ala.

[8] The peptide according to any one of [1] to [7], wherein the number of amino acids is 30 or less.

[9] The peptide according to any one of [1] to [8], having EGFR binding properties.

[10] A pharmaceutical agent comprising the peptide according to any one of [1] to [9] or a labeled product thereof.

[11] A detection agent for a cancer cell or a cancer tissue containing the peptide according to any one of [1] to [9] or a labeled product thereof.

[12] A cancer diagnostic agent containing the peptide according to any one of [1] to [9] or a labeled product thereof.

[13] A cancer therapeutic agent containing the peptide according to any one of [1] to [9] or a labeled product thereof.

[14] The peptide according to anyone of [1] to [9] or a labeled product thereof for detecting a cancer cell or a cancer tissue.

[15] The peptide according to anyone of [1] to [9] or a labeled product thereof for a cancer diagnosis or a cancer treatment.

[16] A use of the peptide according to any one of [1] to [9] or a labeled product thereof for production of a detection agent for a cancer cell or a cancer tissue.

[17] A use of the peptide according to any one of [1] to [9] or a labeled product thereof for production of a cancer diagnostic agent or a cancer therapeutic agent.

[18] A detection method of a cancer cell or a cancer tissue, including a use of the peptide according to any one of [1] to [9] or a labeled product thereof.

[19] A cancer diagnostic method or cancer therapeutic method, including a use of the peptide according to any one of [1] to [9] or a labeled product thereof.

Effects of the Invention

The peptide of the present invention shows specific and high binding properties to EGFR and this peptide or a labeled product thereof is thus useful as a detection agent for cells or tissues expressing EGFR, specifically various cancer cells and cancer tissues, that is, a diagnostic agent for cancer. Furthermore, the peptide of the present invention competitively inhibits binding between EGFR and EGF and is thus useful as therapeutic agent for a cancer expressing EGFR.

BRIEF DESCRIPTION OF DRAWINGS

FIG. 3 shows a peptide sequence displayed by a phage that was collected in 3 rounds of EGFR target panning.

FIG. 9 shows a peptide sequence displayed by an I-1010 alanine substituted phage.

FIG. 10 shows a peptide sequence displayed by an I-1012 alanine substituted phage.

FIG. 11 shows a peptide sequence displayed by an I-1015 alanine substituted phage.

FIG. 15 shows a peptide sequence displayed by an I-1010 amino acid substituted phage.

DETAILED DESCRIPTION OF THE INVENTION

Figure 1:
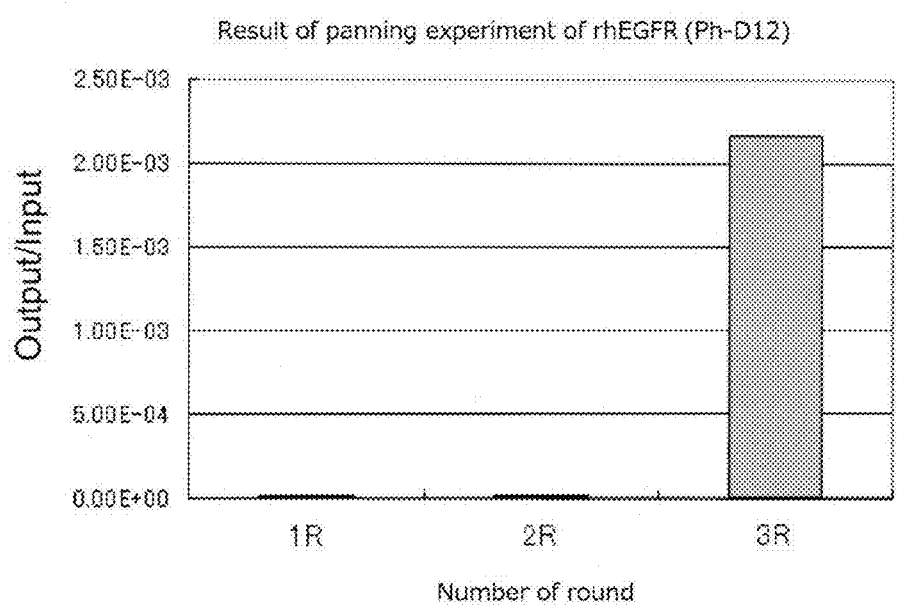
FIG. 1 shows a ratio of an output titer/input titer in a panning experiment with the D12 library.

The peptide of the present invention is a peptide which contains at least the amino acid sequence represented by the formula (1), (2) or (3) and is composed of 12 to 50 amino acids:

$$X^1\text{-His-}X^2\text{-}X^3\text{-Asp-}X^4\text{-}X^5\text{-}X^6\text{-}X^7\text{-}X^8\text{-Trp-His} \quad (1); \text{ (SEQ ID NO: 55)}$$

$$\text{Phe-His-Asp-Trp-}X^{11}\text{-Pro-}X^{12}\text{-}X^{13}\text{-}X^{14}\text{-}X^{15}\text{-}X^{16}\text{-}X^{-17} \quad (2); \text{ (SEQ ID NO: 56)}$$

and $$\text{Leu-His-}X^{21}\text{-Ser-}X^{22}\text{-Trp-Met-}X^{23}\text{-}X^{24}\text{-}X^{25}\text{-}X^{26}\text{-}X^{27} \quad (3). \text{ (SEQ ID NO: 57)}$$

In the above described formula (1), $X^1$ represents Trp or Phe. $X^2$ represents Leu, Met, Ile or Val. $X^3$ represents Ser, Ala, Thr, Gly, Asn, Asp, Glu, Arg or Lys, preferably represents Ser, Ala, Thr, Gly or Asn, and more preferably represents Ser or Ala. $X^4$ represents Leu, Met, Ile, Val, Ala, Phe, Tyr, Trp, His or Cys, preferably represents Leu, Met, Ile, Val or Ala, and more preferably represents Leu or Ala. $X^5$ represents Trp, Phe or Tyr, preferably represents Trp or Phe, and more preferably represents Trp. $X^6$ represents Gln, Asn, Asp, Glu, Ala, Ser, Thr, Leu, Met, Lys or Arg, preferably represents Gln, Asn or Ala, and more preferably represents Gln or Ala. $X^7$ represents Asn, Gln, Asp, Glu, Ser, Thr, Ala, Gly, Lys or Arg, preferably represents Asn, Gln or Ala, and more preferably represents Asn or Ala. $X^8$ represents Ala, Gly, Ser, Thr, Asn, Val or Cys, preferably represents Ala, Gly, Ser or Thr, and more preferably represents Ala.

Among peptides of the formula (1), preferable is a peptide wherein $X^1$ represents Trp or Phe, $X^2$ represents Leu, Met, Ile or Val, $X^3$ represents Ser, Ala, Thr, Gly or Asn, $X^4$ represents Leu, Met, Ile, Val or Ala, $X^5$ represents Trp or Phe, $X^6$ represents Gln, Asn or Ala, $X^7$ represents Asn, Gln or Ala, and $X^8$ represents Ala, Gly, Ser or Thr, which is composed of 12 to 50 amino acids.

Among peptides of the formula (1), more preferable is a peptide wherein $X^1$ represents Trp or Phe, $X^2$ represents Leu, Met, Ile or Val, $X^3$ represents Ser or Ala, $X^4$ represents Leu or Ala, $X^5$ represents Trp, $X^6$ represents Gln or Ala, $X^7$ represents Asn or Ala, and $X^8$ represents Ala, which is composed of 12 to 50 amino acids.

In the above described formula (2), $X^{11}$ represents Leu, Met, Ile, Val, Ala, Phe, Tyr, Trp, His or Cys, preferably represents Leu, Met, Ile, Val or Ala, and more preferably represents Leu or Ala. $X^{12}$ represents Glu, Asp, Gln, Asn, Ala, Ser, Thr, Lys, Arg or His, preferably represents Glu, Asp, Gln, Asn or Ala, and more preferably represents Glu or Ala. $X^{13}$ represents Val, Ala, Leu, Ile, Met, Thr, Cys or Asn, preferably represents Val, Ala, Leu or Ile, and more preferably represents Val or Ala. $X^{14}$ represents Ser, Ala, Thr, Gly, Asn, Asp, Glu, Arg or Lys, preferably represents Ser, Ala, Thr, Gly or Asn, and more preferably represents Ser or Ala. $X^{15}$ represents Pro, Val, Ile, Lys, Ala, Met, Trp, Tyr, Ser, Thr, Cys or Phe, preferably represents Pro, Val, Ile or Ala, and more preferably represents Pro or Ala. $X^{16}$ represents Pro, Val, Ile, Lys, Ala, Met, Trp, Tyr, Ser, Thr, Cys or Phe, preferably represents Pro, Val, Ile or Ala, and more preferably represents Pro or Ala. $X^{17}$ represents Asp, Glu, Asn, Gln, Ala, Ser, Thr, Lys, Arg or His, preferably represents Asp, Glu, Asn, Gln or Ala, and more preferably represents Asp or Ala.

Among peptides of the formula (2), preferable is a peptide wherein $X^{11}$ represents Leu, Met, Ile, Val or Ala, $X^{12}$ represents Glu, Asp, Gln, Asn or Ala, $X^{13}$ represents Val, Ala, Leu or Ile, $X^{14}$ represents Ser, Ala, Thr, Gly or Asn, $X^{15}$ represents Pro, Val, Ile or Ala, $X^{16}$ represents Pro, Val, Ile or Ala, and $X^{17}$ represents Asp, Glu, Asn, Gln or Ala, which is composed of 12 to 50 amino acids.

Among peptides of the formula (2), more preferable is a peptide wherein $X^{11}$ represents Leu or Ala, $X^{12}$ represents Glu or Ala, $X^{13}$ represents Val or Ala, $X^{14}$ represents Ser or Ala, $X^{15}$ represents Pro or Ala, $X^{16}$ represents Pro or Ala, and $X^{17}$ represents Asp or Ala, which is composed of 12 to 50 amino acids.

In the above described formula (3), $X^{21}$ represents Gln, Asn, Asp, Glu, Ala, Ser, Thr, Leu, Met, Lys or Arg, preferably represents Gln, Asn or Ala, and more preferably represents Gln or Ala. $X^{22}$ represents Glu, Asp, Gln, Asn, Ala, Ser, Thr, Lys, Arg or His, preferably represents Glu, Asp, Gln or Ala, and more preferably represents Glu or Ala. $X^{23}$ represents Tyr, Phe, Trp, His, Leu, Met, Ile, Val, Cys or Ala, preferably represents Tyr, Phe, Trp, His or Ala, and more preferably represents Tyr or Ala. $X^{24}$ represents Val, Ala, Leu, Ile, Met, Thr, Cys or Asn, preferably represents Val, Ala, Leu or Ile, and more preferably represents Val or Ala. $X^{25}$ represents Asp, Glu, Asn, Gln, Ala, Ser, Thr, Lys, Arg or His, preferably represents Asp, Glu, Asn, Gln or Ala, and more preferably represents Asp or Ala. $X^{26}$ represents Ile, Val, Leu, Met, Ala, Phe, Tyr, Trp or Gly, preferably represents Ile, Val, Leu, Met or Ala, and more preferably represents Ile or Ala. $X^{27}$ represents His, Tyr, Phe, Lys, Arg, Leu, Met or Ala, preferably represents His, Tyr, Phe, Lys, Arg or Ala, and more preferably represents His or Ala.

Among peptides of the formula (3), preferable is a peptide wherein $X^{21}$ represents Gln, Asn or Ala, $X^{22}$ represents Glu, Asp, Gln or Ala, $X^{23}$ represents Tyr, Phe, Trp, His or Ala, $X^{24}$ represents Val, Ala, Leu or Ile, $X^{25}$ represents Asp, Glu, Asn, Gln or Ala, $X^{26}$ represents Ile, Val, Leu, Met or Ala, and $X^{27}$ represents His, Tyr, Phe, Lys, Arg or Ala, which is composed of 12 to 50 amino acids.

Among peptides of the formula (3), more preferable is a peptide wherein $X^{21}$ represents Gln or Ala, $X^{22}$ represents Glu or Ala, $X^{23}$ represents Tyr or Ala, $X^{24}$ represents Val or Ala, $X^{25}$ represents Asp or Ala, $X^{26}$ represents Ile or Ala, and $X^{27}$ represents His or Ala, which is composed of 12 to 50 amino acids.

In addition, the number of amino acids in the peptide of the present invention is from 12 to 50, the upper limit of the amino acid number is preferably 40, more preferably 30, further more preferably 20, and particularly preferably 18. Note that an optional amino acid may be added in either side of the N terminal or the C terminal in the formula (1), (2) or (3).

Substitutions of $X^1$ to $X^8$, $X^{11}$ to $X^{17}$ and $X^{21}$ to $X^{27}$ in the peptide of the present invention are based on showing the same activity when the substitutions are conservative substitution and semi-conservative substitution as a result of binding property tests described in examples below. Herein, typical conservative substitution and semi-conservative substitution are shown in table 1.

TABLE 1

| Amino acids | Conservative substitution | Semi-conservative substitution |
| --- | --- | --- |
| A(Ala) | G(Gly); S(Ser); T(Thr) | N(Asn); V(Val); C(Cys) |
| C(Cys) | A(Ala); V(Val); L(Leu) | M(Met); I(Ile); F(Phe); G(Gly) |
| D(Asp) | E(Glu); N(Asn); Q(Gln) | A(Ala); S(Ser); T(Thr); K(Lys); R(Arg); H(His) |
| E(Glu) | D(Asp); Q(Gln); N(Asn) | A(Ala); S(Ser); T(Thr); K(Lys); R(Arg); H(His) |
| F(Phe) | W(Trp); Y(Tyr); L(Leu); M(Met); H(His) | I(Ile); V(Val); A(Ala) |
| G(Gly) | A(Ala) | S(Ser); N(Asn); T(Thr); D(Asp); E(Glu); N(Asn); Q(Gln) |
| H(His) | Y(Tyr); F(Phe); K(Lys); R(Arg) | L(Leu); M(Met); A(Ala) |
| I(Ile) | V(Val); L(Leu); M(Met); A(Ala) | F(Phe); Y(Tyr); W(Trp); G(Gly) |
| K(Lys) | R(Arg); H(His) | D(Asp); E(Glu); N(Asn); Q(Gln); S(Ser); T(Thr); A(Ala) |
| L(Leu) | M(Met); I(Ile); V(Val); A(Ala) | F(Phe); Y(Tyr); W(Trp); H(His); C(Cys) |
| M(Met) | L(Leu); I(Ile); V(Val); A(Ala) | F(Phe); Y(Tyr); W(Trp); C(Cys) |
| N(Asn) | Q(Gln) | D(Asp); E(Glu); S(Ser); T(Thr); A(Ala); G(Gly); K(Lys); R(Arg) |
| P(Pro) | V(Val); I(Ile) | L(Leu); A(Ala); M(Met); W(Trp); Y(Tyr); S(Ser); T(Thr); C(Cys); F(Phe) |
| Q(Gln) | N(Asn) | D(Asp); E(Glu); A(Ala); S(Ser); T(Thr); L(Leu); M(Met); K(Lys); R(Arg) |
| R(Arg) | K(Lys); H(His) | N(Asn); Q(Gln); S(Ser); T(Thr); D(Asp); E(Glu); A(Ala) |
| S(Ser) | A(Ala); T(Thr); G(Gly); N(Asn) | D(Asp); E(Glu); R(Arg); K(Lys) |
| T(Thr) | A(Ala); S(Ser); G(Gly); N(Asn); V(Val) | D(Asp); E(Glu); R(Arg); K(Lys); I(Ile) |
| V(Val) | A(Ala); L(Leu); I(Ile) | M(Met); T(Thr); C(Cys); N(Asn) |
| W(Trp) | F(Phe); Y(Tyr); H(His) | L(Leu); M(Met); I(Ile); V(Val); C(Cys) |
| Y(Tyr) | F(Phe); W(Trp); H(His) | L(Leu); M(Met); I(Ile); V(Val); C(Cys) |

The peptide of the present invention can be produced by a recombinant technique using DNA coding for the above described amino acid sequences, and also can be produced by a peptide synthesis method in organic synthetic chemistry. The peptide synthesis method in organic synthetic chemistry is conducted by means of protection of general functional groups, activation of a carboxyl group, formulation of peptide binding, and deprotection of a protecting group. These reactions are preferably carried out by a solid phase method.

Among the peptides of the present invention, peptides expressed by SEQ ID Nos. 2, 4 and 7 (I-1010, I-1012 and I-1015) can be selected from a phage library that displays random peptide sequences by screening peptides having binding properties to EGFR in a phage display method. D12 is preferable as a phage used in the phage display method. In order to select a peptide that strongly binds to EGFR from a phage library, a phage group is incubated with EGFR, a phase which did not bind to EGFR is washed away and then a phage which bound to the EGFR is collected. To find out what sequence in a peptide that the collected phage displays, the corresponding part of the phage genome may be sequenced. When interaction between EGFR and a peptide is not very strong, a phage having weak binding force strings along as the background. Accordingly, after a series of flow of binding→washing→recovery, phages are infected with Escherichia coli once again to prepare a secondary library, and a panning operation of repeating a series of the operations is carried out once again using this library. In the library obtained by repetition of panning, the number of phages having high binding ability to EGFR increases. In this way, a desired phage having a high binding property to EGFR can be selected.

The peptide of the present invention specifically binds to EGFR. Therefore, the peptide of the present invention or a labeled product thereof is useful as a reagent for detecting EGFR or a cell or a tissue which expresses EGFR. Herein, a labeled product of the peptide of the present invention may be a labeled product capable of detecting a peptide binding to EGFR and examples thereof include radioactive isotopes, affinity labeling (e.g., biotin and Avidin), enzyme labeling (e.g., horseradish peroxidase and alkaline phosphatase), fluorescence labeling (e.g., FITC and rhodamine), and paramagnetic atoms. Among these labeled products, fluorescence labeling and labeling with a positron nucleus are preferable for detecting cancer cells or cancer tissues which express EGFR, for example, colon cancer.

A labeled product of the peptide of the present invention is useful for a diagnosis of cancer expressing EGFR, for example, an earlier cancer diagnosis. For instance, in a diagnosis for the purpose of confirming presence or absence of existence of a cancer tissue, a site to be treated is brought into contact with, for example, the above described fluorescence labeled peptide by means of dusting, injection, or the like, and an excessive fluorescent component was then removed by a washing treatment, thereafter irradiating the site to be treated with an exciting light, and presence or absence of a fluorescence stained tissue can be thus confirmed with the naked eye or a microscope.

As a preferable embodiment, the fluorescence labeled peptide of the present invention is used for a cancer diagnosis by an endoscope as a fluorescent contrast agent; for example, the fluorescence labeled peptide is endoscopically brought into contact with a tissue by means of dusting, or the like, thereafter conducting a washing treatment, the site to be treated is irradiated with an exciting light from the endoscopic light source, and presence or absence of a fluorescence stained tissue may be endoscopically confirmed. Accordingly, the fluorescence labeled peptide can be used not only for a diagnosis of discovering early stage cancer but also for staining a site which is generally suspected of a pathologic lesion endoscopically to judge a border between the pathologic lesion site and a non-pathologic lesion site from presence or absence of fluorescence by magnifying fluorescence observation. A kind of an endoscope is not particularly limited, and a fluorescence endoscope capable of irradiation of an exciting light for fluorescein as the endoscopic light source or a confocal endoscope additionally having magnifying power is preferable.

In addition, as a modifying fluorescent dye, not only fluorescein but also, for example, a fluorescent dye with a different excitation wavelength such as an cyanine compound may be used. When a cyanine compound such as indocyanine green is used as a fluorescer, an excitation wavelength thereof further shifts to the long wavelength range as compared to fluorescein and, therefore, a cyanine compound is effective for confirmation of a pathologic lesion in a deeper part. When a positron nucleus is modified to the peptide of the present invention, a pathologic lesion site can be detected by PET, SPECT, or the like. When gadolinium is modified to the peptide of the present invention, a pathologic lesion site can be detected by MRI. Accordingly, the peptide of the present invention can be utilized not only in cancer in a site capable of being reached endoscopically such as mainly digestive organs but also in cancerous lesions in the entire body.

Furthermore, the peptide of the present invention or a labeled product thereof competitively inhibits binding between EGFR and EGF and therefore can also be used not only in detection of cancer cells and cancer diagnoses as described above but also in cancer treatments.

Cells or tissues capable of detection, diagnoses, treatments by the peptide of the present invention may be cells or tissues expressing EGFR, and examples thereof include cancer cells or cancer tissues of, specifically, non-small-cell lung cancer, breast cancer, squamous cell carcinoma of the head and neck (SCCHN), colon cancer, stomach cancer, esophageal cancer, ovarian cancer, prostate cancer, urinary bladder cancer, kidney cancer, and the like.

The peptide of the present invention or a labeled product thereof is used as a cancer detection agent, a cancer diagnostic agent or a cancer therapeutic agent, the peptide of the present invention or a labeled product thereof can be directly used and also formed into a composition suitable for various administration forms with pharmaceutically acceptable carriers. Examples of the composition include an injectable agent, an epipastic agent, an oral administration agent, and a transrectal agent. Examples of the pharmaceutically acceptable carriers include water, serine solution, various buffers, vehicles, disintegrating agents, binding agents and lubricants.

An administration amount in the case of using the peptide of the present invention or a labeled product thereof as a cancer therapeutic agent differs depending on symptoms, body weight, and the like, is generally preferably from 0.1 mg to 1000 mg for an adult per day.

EXAMPLES

Next, the present invention will be specifically explained by reference to examples; however, the present invention is not limited to these examples.

Example 1 (Phage Display)

[Procedure]
1. Panning Experiment—Round 1
5 µg/mL-Recombinant human IgG$_1$ Fc (rhIgG$_1$, R&D Systems) and recombinant human EGFR/Fc chimera (rhEGFR, R&D Systems) were individually added to a 96-well plate in each amount of 200 µL (1 µg/well), and stood still and incubated at 4° C. overnight (forming a solid phase on the plate). A non-solid phase protein in the wells was removed, thereto was added a blocking buffer (5 mg/mL BSA (bovine serum albumin)/TBS (50 mM Tris-HCl/150 mM NaCl)) in an amount of 300 µL/well, the mixture was stool still and incubated at 37° C. for 1 hour and then washed three times with 200 µL/well of 0.1% TBST (0.1% Tween 20/TBS).

100 µL of 0.1% TBST was added to the rhIgG$_1$ solid phase well and a D12 phage library (1×10$^{13}$ PFU/mL) and a C7C phage library (2×10$^{13}$ PFU/mL) were added thereto in each amount of 10 µL. Herein, 200 µl of 0.1% TBST was added to the rhEGFR solid phase well for the purpose of prevention of dryness.
*PFU: Plaque Forming Units Two kinds of peptide displaying phage libraries (NEW ENGLAND BioLabs Inc.) were used, and the D12 library displays a linear random peptide with 12 residues and is a phage library having 2.7×10$^9$ kinds of different peptide sequences. The C7C library displays a cyclic random peptide with 7 residues and is a phage library having 1.2×10$^9$ kinds of different peptide sequences.

Shaking incubation was carried out using a seesaw-shaker at room temperature for 1 hour, for the purpose of removing a peptide displayed phage (hereafter abbreviated as a phage) that is assumed to bind to a Fc site of a rhEGFR, the phage was allowed to bind to rhIgG$_1$ formed into a solid phase and the phage solution was then removed and washed 10 times with 200 µL/well of 0.1% TBST. 100 µL of 1 mg/mL-BSA/0.2 M glycine-HCl (pH 2.2) was added thereto and shaking incubation was carried out at room temperature for 10 minutes to elute the phage. The eluate was collected and 15 µL of 1 M Tris-HCl (pH 9.1) was added to the collected solution to neutralize the solution. The titer of the phage was measured using a part of the collected eluate.

2. Amplification of Collected Phage

The phage eluate obtained in the operation 1 was infected to ER2738 bacteria [F'lacI$^q$Δ(lacZ)M15 proA$^+$B$^+$zzf:Tn10 (Tet$^R$)/fhuA2 supE thiΔ (lac-proAB) Δ (hs-dMS-mcrB) 5 (r$_k^-$m$_k^-$McrBC$^-$)] in a logarithmic growth phase in 20 mL of LB and incubated for 4 hours and 30 minutes while intensively stirring at 37° C. by use of a shaking incubator. 50 mL of a phage infected bacterial culture liquid was transferred into a centrifugal tube and the above described sample was centrifuged at 4° C. by 8,900×g for 10 minutes using a high speed refrigerated centrifuge. After centrifugation, the supernatant was collected into a new tube for the purpose of removing the ER2738 bacteria. 3.6 mL (⅕ amount) of a PEG/NaCl (20% polyehtylene glycol 6,000, 2.5 M NaCl) solution was added to the collected phage solution and the mixture was well stirred and incubated at 4° C. for 16 hours to precipitate a phage. In order to recover the precipitated phage, the mixture was centrifuged at 4° C. by 8,900×g for 10 minutes by a high speed refrigerated centrifuge to remove the supernatant. For the purpose of completely removing the supernatant, the mixture was centrifuged once again to remove the supernatant. 1 mL of TBS cooled with ice was added to the precipitated phage, and the mixture was suspended and transferred into a microtube. The phage suspension was centrifuged at 4° C. by 16,000×g for 5 minutes by use of a high speed refrigerated centrifuge. The supernatant was collected to another tube and the residue that was not suspended was removed, and 200 µL of PEG/NaCl was added to the collected solution and stirred with a mixer. The above described solution was incubated on ice for 1 hour to precipitate a phage. The solution was centrifuged at 4° C. by 16,000×g for 10 minutes using a high speed refrigerated centrifuge to precipitate the phage and the supernatant was removed. This centrifugation step was carried out once again and the supernatant was completely removed. 200 µL of 0.02% NaN$_3$ (Wako)/TBS was added to the obtained phage precipitate and completely suspended, the suspension was centrifuged at 4° C. by 16,000×g for 5 minutes by a high speed refrigerated centrifuge, and the supernatant was collected to thus remove the residue that was not suspended. The titer of the collected phage concentrated solution was measured.

3. Panning Experiment—Rounds 2 and 3

The second and third panning experiments were carried out using the concentrated phage solution. In the second panning experiment, different points from the first operation lie in that an added phage amount was 2×10$^{11}$ PFU/well and the washing solution was 0.3% TBST (0.3% Tween20/TBS). In the third panning experiment, different points from the first operation lie in that an added phage amount was 2×10$^{11}$ PFU/well and the washing solution was 0.5% TBST (0.5% Tween20/TBS).

4. Measurement of Titer

ER2738 bacteria were cultured in 3 mL of LB until a logarithmic growth phase (OD600; to 0.5) and 200 μL of the ER2738 culture solution was added with 10 μL of a phage solution diluted to have a required concentration. This mixed solution was well stirred with a mixer and incubated at room temperature for 5 minutes, and then mixed with 4 mL of a dissolved top ager solution to be inoculated on an LB/IPTG/Xgal plate.

The phage infected *Escherichia coli* inoculated plate was incubated at 37° C. for 16 hours and the number of the obtained blue plaques was counted. The phage number was calculated using a phage dilution ratio (count plaque number×dilution ratio/10 μL).

[Result]

Figure 2:
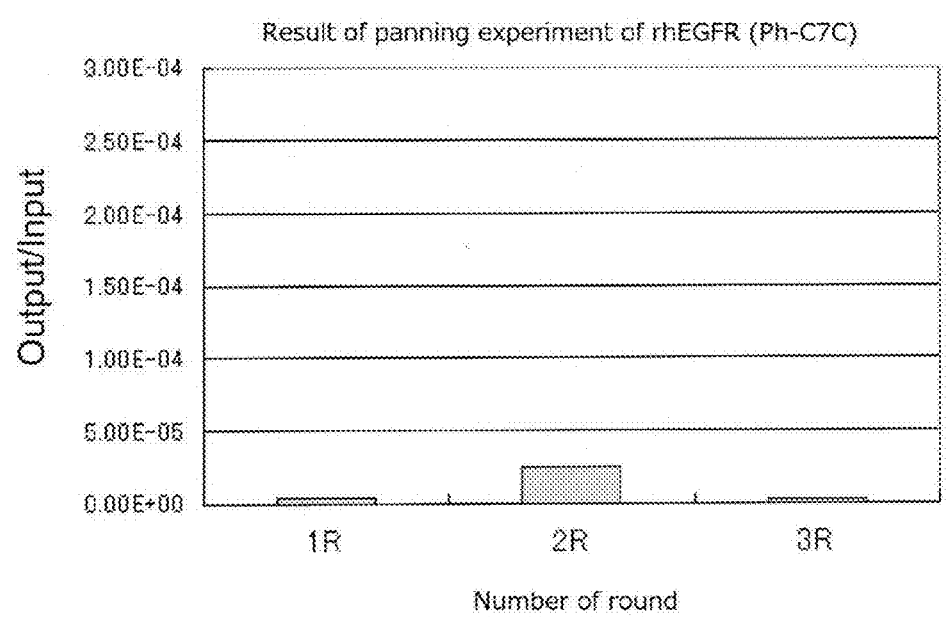
FIG. 2 shows a ratio of an output titer/input titer in a panning experiment with the C7C library.

Regarding changes in values of a ratio of an input titer (phage titer added to a target molecule) and an output titer (phage titer eluted from a target molecule after washing) in an experiment using a phage library, the result of the D12 library is shown in FIG. 1 and the result of the C7C library is shown in FIG. 2.

As a result that the rhEGFR target panning experiment using the D12 library proceeded to the 3rd round, when ratios of output titers/input titers were compared, the ratio of the 3rd round was observed to increase about 130 times as high as that of the 2nd round. It was therefore prospected that a phage showing rhEGFR specific binding properties was selected.

Although rhEGFR target panning experiment using the C7C library proceeded to the 3rd round, increase in a ratio of an output titer/input titer was not observed.

Example 2 (Sequence Analysis)

[Procedure]

A phage obtained in three rounds of the panning experiment using the D12 library was cloned according to a general method (Phage Display A Laboratory Manual, Cole Spring Harbor Laboratory Press, 2001) and the basic sequence of the phage displayed peptide part was determined. The determination of the basic sequence was made by a dideoxy termination method using a primer [−96gIII sequencing primer (5'-$^{HO}$CCCTCATAGTTAGCGTAACG-3') (SEQ ID No. 1), S1259A, NEB] which corresponds to a complementary strand of a basic sequence located in the downstream of 96 residues from the displayed peptide region. For migration of a reaction product and data analysis, a capillary sequencer was used.

[Result]

Displayed peptide sequences predicted from the determined basic sequences are shown in FIG. 3.

Among the sequences, the obtained I-1010 phage displayed peptide sequence (SEQ ID No. 2) had 6 clones having the same sequence in 15 clones that were examined in the three rounds (40%). Furthermore, two clones of each of I-1012 phage (SEQ ID No. 4) and I-1015 phage (SEQ ID No. 7) were obtained (13.3%). Only one clone of each of I-1011 phage (SEQ ID No. 3), I-1013 phage (SEQ ID No. 5), I-1014 phage (SEQ ID No. 6), I-1016 phage (SEQ ID No. 8), and I-1017 phage (SEQ ID No. 9) was obtained.

Therefore, it was revealed that while the number of panning proceeded, an I-1010 phage, I-1012 phage and I-1015 phage were selected. The reason of selection of specific phage clones is because the phage clones show high binding properties to a target molecule.

Example 3 (Test of Phage Binding Property (Condition of Formulation of Protein Solid Phase-1))

[Procedure]

A rhEGFR that is a target protein, rhIgG$_1$ that is a rhEGFR-labeled Fc moiety, and BSA as a standard protein were added to a 96-well microplate to be 1 μg/well, and stood still at 4° C. overnight to be thus formed into a solid phase. A protein solution was removed, 300 μl of a blocking buffer was added and the mixture was incubated at 37° C. for 1 hour to thus block the wells. After removal of the blocking buffer, the wells were washed with 200 μl of 0.5% TBST being the washing solution three times and thereto was finally added 100 μl of 0.5% TBST. An amplification phage solution (I-1010, I-1012 and I-1015 phages and M13KE (peptide non-displayed phage)) was added to the above described wells to have 1×10$^{10}$ PFU and mixed by pipetting. In the reaction, the mixture was gently shaken at room temperature for 1 hour. The reaction solution was removed and the wells were washed with 200 μl of 0.5% TBST ten times, 100 μl of 0.2 M glycine-HCl (pH 2.2) was added to the wells and stirred by pipetting, thereafter gently shaking at room temperature for 10 minutes. The eluate was collected to a microtube from the wells and added with 15 μl of 1 M Tris-HCl (pH 9.1) to be neutralized and a target binding phage solution was thus obtained. The binding ability of the collected phage was examined by a measurement of a titer.

[Result]

Figure 4:
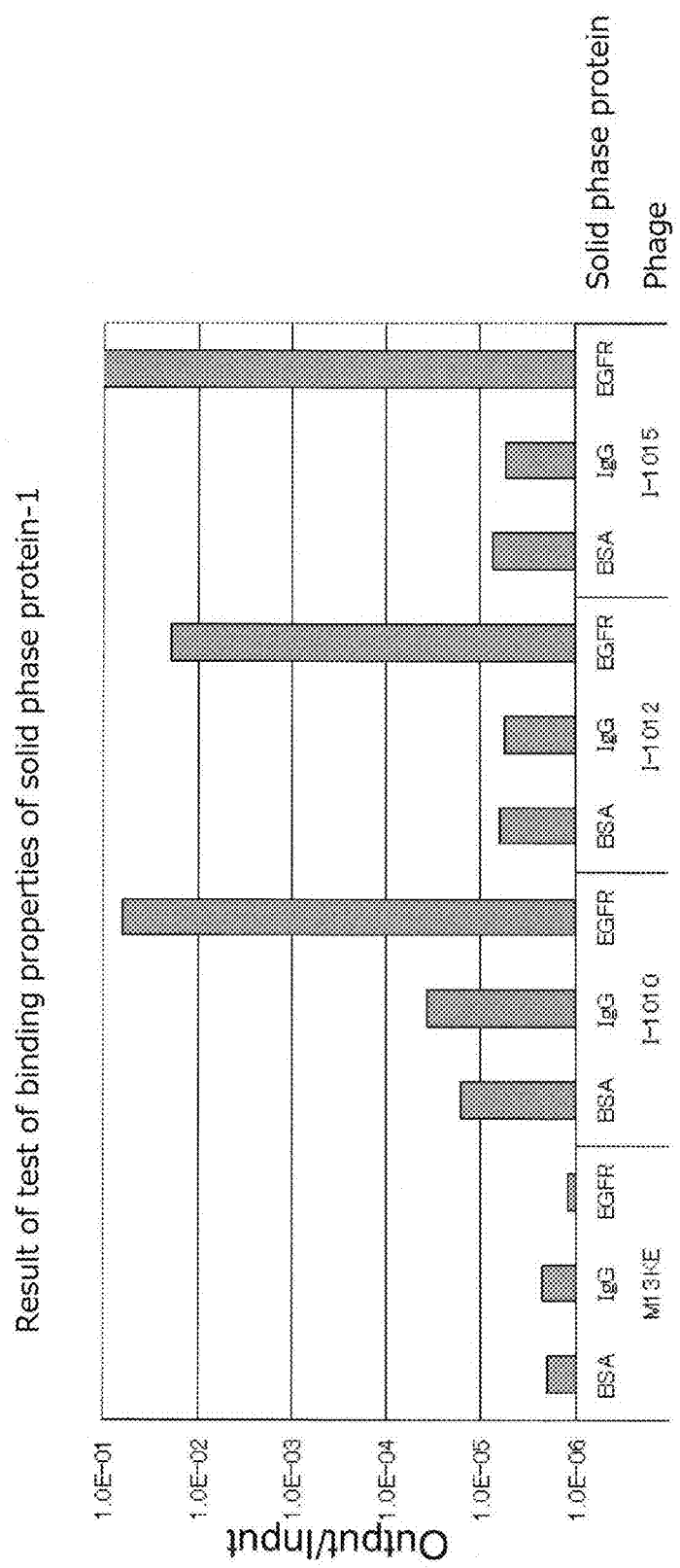
FIG. 4 shows a result of a binding property test of I-1010, I-1012 and I-1015 phages to a solid phase protein.

FIG. 4 shows a ratio of an input titer/output titer of the binding property test by a solid phase formulation method using I-1010, I-1012 and I-1015 phages.

It was revealed that the binding property of the I-1010 phage to a rhEGFR is 1665 times as high as that to rhIgG$_1$ being an Fc moiety and 3809 times as high as that to BSA being a standard protein.

It was revealed that the binding property of the I-1012 phage to a rhEGFR was 3420 times as high as that to rhIgG$_1$ being an Fc moiety and 3095 times as high as that to BSA being a standard protein.

It was revealed that the binding property of the I-1015 phage to a rhEGFR was 19018 times as high as that to rhIgG$_1$ being an Fc moiety and 13964 times as high as that to BSA being a standard protein.

A gap of binding properties among proteins formed into solid phases was not observed in the M13KE phage and any value was low.

It was revealed from the result of FIG. 4 that the I-1010, I-1012, and I-1015 phages specifically bind to a rhEGFR in the conditions of formulation of protein solid phases.

In addition, as binding properties of the I-1010 phage and the M13KE phage to a rhEGFR were compared, it was revealed that the I-1010 phage was 52235 times higher. Furthermore, binding of the I-1012 phage to a rhEGFR was 16301 times higher and binding of the I-1015 phage to a rhEGFR was 86592 times higher as compared to that of the M13KE phage. It was shown from this result that peptide sequences displayed by the I-1010, I-1012 and I-1015 phages are involved with binding to a rhEGFR.

Example 4 (Phage Binding Property Test (Conditions of Formulation of Protein Solid Phase-2))

[Procedure]

A rhEGFR that is a target protein, a recombinant human ErbB2 (rhErbB2, PROSPEC) as a HER2 protein belonging to the ErbB family same as an EGFR, are combinant human IGF-1R, CF (rhIGF-1R, R&D Systems) as an IGF-1R protein that is one of extracellular proteins were added to a 96-well microplate to be 1 μg/well, and stood still at 4° C. overnight to be thus formed into a solid phase. A protein solution was removed, 300 μl of a blocking buffer was added and the mixture was incubated at 37° C. for 1 hour to thus block the wells. After removal of the blocking buffer, the wells were washed three times with 200 μl of 0.5% TBST washing solution, and finally 100 μl of 0.5% TBST was added thereto. An amplification phage solution (I-1010, I-1012 and I-1015 phages and M13KE (peptide non-displayed phage)) was added to the above described wells to have $1 \times 10^{10}$ PFU and mixed by pipetting. In the reaction, the mixture was gently shaken at room temperature for 1 hour. The reaction solution was removed, the wells were washed with 200 μl of 0.5% TEST ten times, and 100 μl of 0.2 M glycine-HCl (pH 2.2) was then added to the wells and stirred by pipetting, thereafter gently shaking at room temperature for 10 minutes. The eluate was collected to a microtube from the wells and added with 15 μl of 1 M Tris-HCl (pH 9.1) to be neutralized and a target binding phage solution was thus obtained. The binding ability of the collected phage was examined by a measurement of a titer.

[Result]

Figure 5:
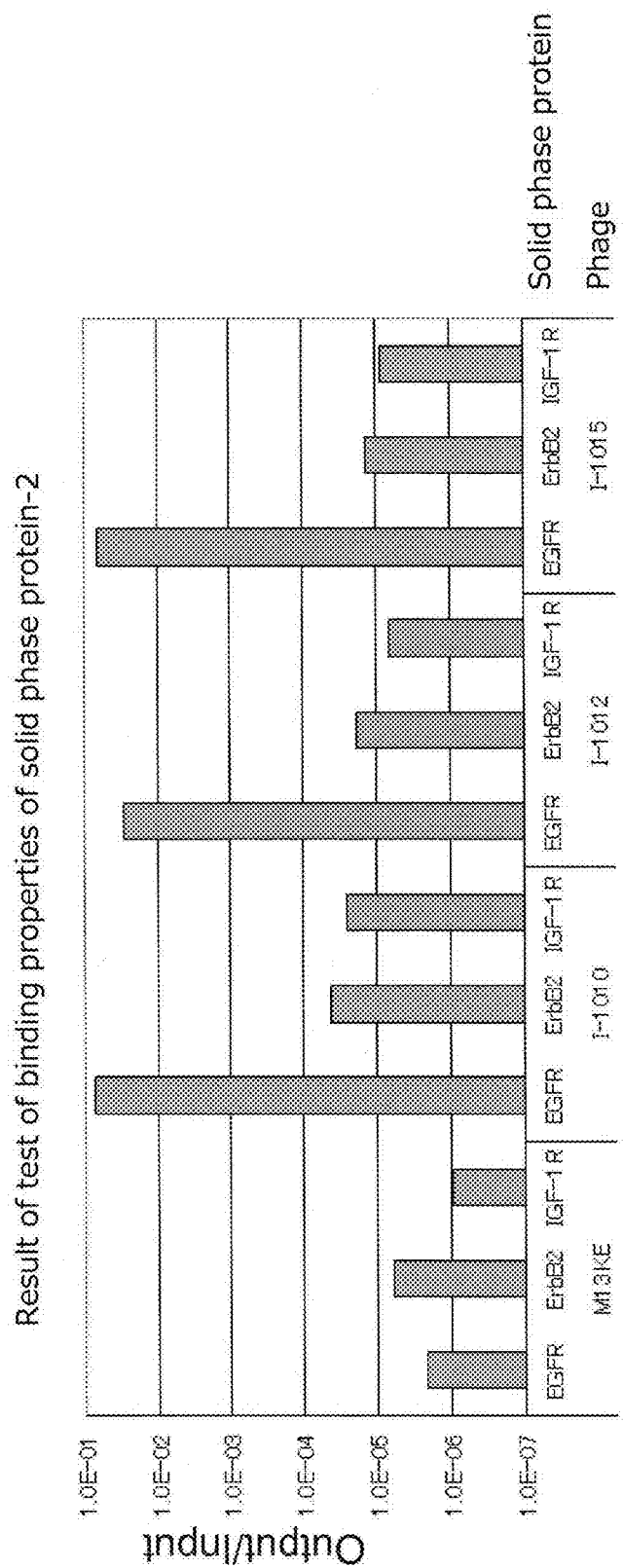
FIG. 5 shows a result of a binding property test of I-1010, I-1012 and I-1015 phages to a solid phase protein.

FIG. 5 shows a ratio of an input titer/output titer of the binding property test by a solid phase formulation method using I-1010, I-1012 and I-1015 phages. A result of the M13KE phage as comparison is also shown in FIG. 5.

It was revealed that the binding property of the I-1010 phage to a rhEGFR was 1764 times as high as that to rhErbB2 and 2827 times as high as that to a rhIGF-1R.

It was revealed that the binding property of the I-1012 phage to a rhEGFR was 1581 times as high as that to rhErbB2 and 4345 times as high as that to a rhIGF-1R.

It was revealed that the binding property of the I-1015 phage to a rhEGFR was 4745 times as high as that to rhErbB2 and 7708 times as high as that to a rhIGF-1R.

A gap of binding properties among proteins formed into solid phases was not observed in the M13KE phage and any value was low.

It was revealed from the result of FIG. 5 that the I-1010, I-1012, and I-1015 phages specifically bind to a rhEGFR in the conditions of formulation of protein solid phases.

In addition, as binding properties of the I-1010 phage and the M13KE phage to a rhEGFR were compared, it was revealed that the I-1010 phage was 34439 times higher. Furthermore, binding of the I-1012 phage to a rhEGFR was 13934 times higher and binding of the I-1015 phage to a rhEGFR was 30806 times higher as compared to that of the M13KE phage. It was shown from this result that peptide sequences displayed by the I-1010, I-1012 and I-1015 phages are involved with binding to a rhEGFR.

Example 5 (Competition Test)

[Procedure]

A rhEGFR that is a target protein was added to a 96-well microplate to be 1 μg/well, and stood still at 4° C. overnight to be thus formed into a solid phase. A protein solution was removed, 300 μl of a blocking buffer was added and the mixture was incubated at 37° C. for 1 hour to thus block the wells. After removal of the blocking buffer, the wells were washed three times with 200 μl of 0.5% TBST washing solution, and finally 100 μl of 0.5% TBST was added thereto. An amplification I-1010 phage solution was added to the above described wells to have $1 \times 10^{10}$ PFU and, subsequently, a synthetic peptide Pep055 (purity 89%, HPLC grade, Hokkaido System Science Co., Ltd.) which was obtained by artificially synthesizing the I-1010 phage displayed peptide (SEQ ID No. 2) was added to have each concentration and a synthetic peptide Pep018 (GAASR-TYLHELI: SEQ ID No. 10) (purity 90%<, HPLC grade, AnyGen, Korea) which is irrelevant to binding to a rhEGFR was added to have each concentration by pipetting. A reaction only of the I-1010 phage without adding both of the peptides was employed as a control. Similar to the I-1010 phage peptide, a synthetic peptide (SEQ ID No. 4) Pep056 (purity 86.7%, HPLC grade, Hokkaido System Science Co., Ltd.) of the I-1012 phage displayed peptide, a synthetic peptide (SEQ ID No. 7) Pep057 (purity 83.7%<, HPLC grade, Hokkaido System Science Co., Ltd.) of the I-1015 phage displayed peptide were also used. In the reaction, the mixture was gently shaken at room temperature for 1 hour. The reaction solution was removed and the wells were washed with 200 μl of 0.5% TBST ten times. 100 μl of 0.2 M glycine-HCl (pH 2.2) was then added to the wells and stirred by pipetting, thereafter gently shaking at room temperature for 10 minutes. The eluate was collected to a microtube from the wells and added with 15 μl of 1M Tris-HCl (pH 9.1) to be neutralized and a target binding phage solution was thus obtained. The binding ability of the collected phage was examined by a measurement of a titer.

[Result]

Figure 6:
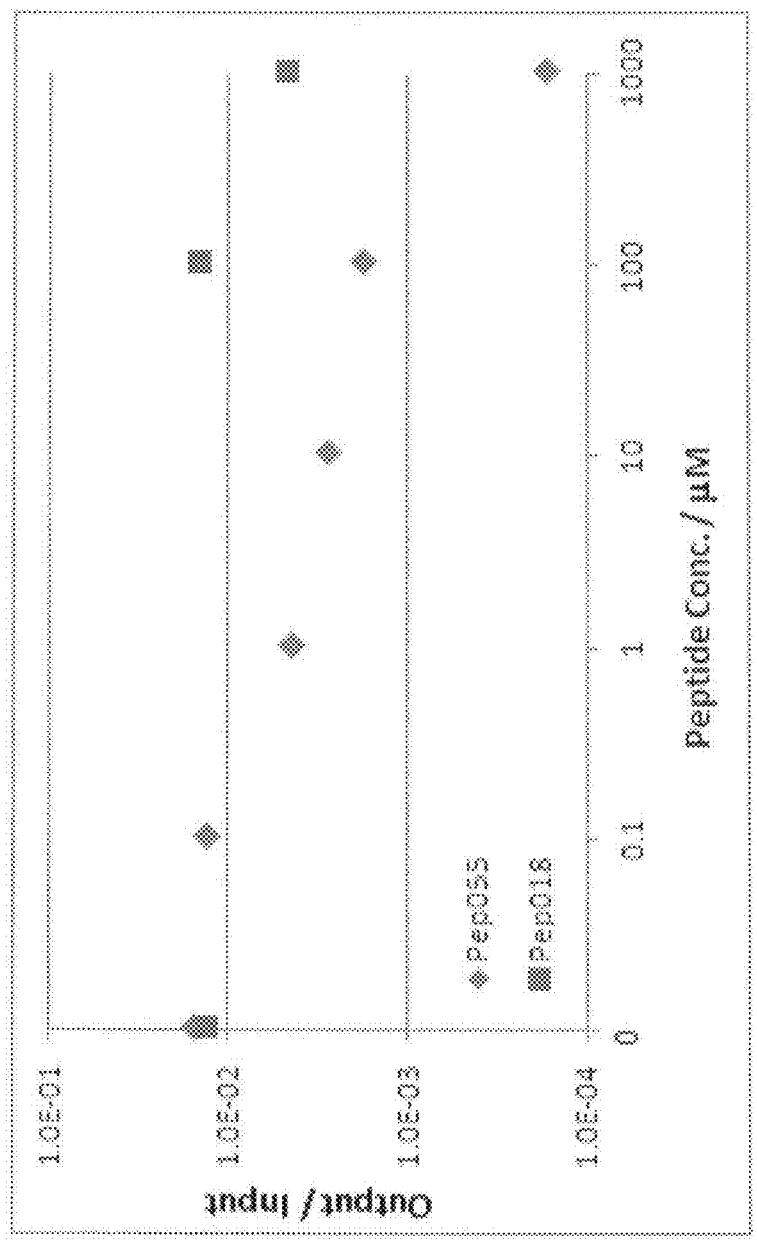
FIG. 6 shows a result of a competition test between I-1010 phage and peptide Pep055 or peptide Pep018.

FIG. 6 shows changes in values of ratios of input titers/output titers of an I-1010 phage and Pep055 in the competition test and a result of the I-1010 phage and Pep018.

As found from FIG. 6, it was revealed that a ratio of an input titer/output titer of the I-1010 phage was dropped on the downside from the time when 1 μM of Pep055 was added and binding of the I-1010 phage to a rhEGFR was inhibited concentration-dependently. However, a high value of a ratio of an input titer/output titer of the I-1010 phage in the case of adding Pep018 was maintained even when Pep018 was added at a concentration of 100 μM.

Pep018 is not involved with binding of the I-1010 phage to an EGFR and therefore decrease of a ratio of an input titer/output titer of the I-1010 phage was not observed even at a high concentration. While, it was revealed that a synthetic peptide Pep055 having a peptide sequence displayed by the I-1010 phage inhibited binding of the I-1010 phage to EGFR concentration-dependently. It can be considered from this result that even though the I-1010 phage displayed peptide is single, the peptide binds to the same site where the I-1010 phage binds to a rhEGFR.

Figure 7:
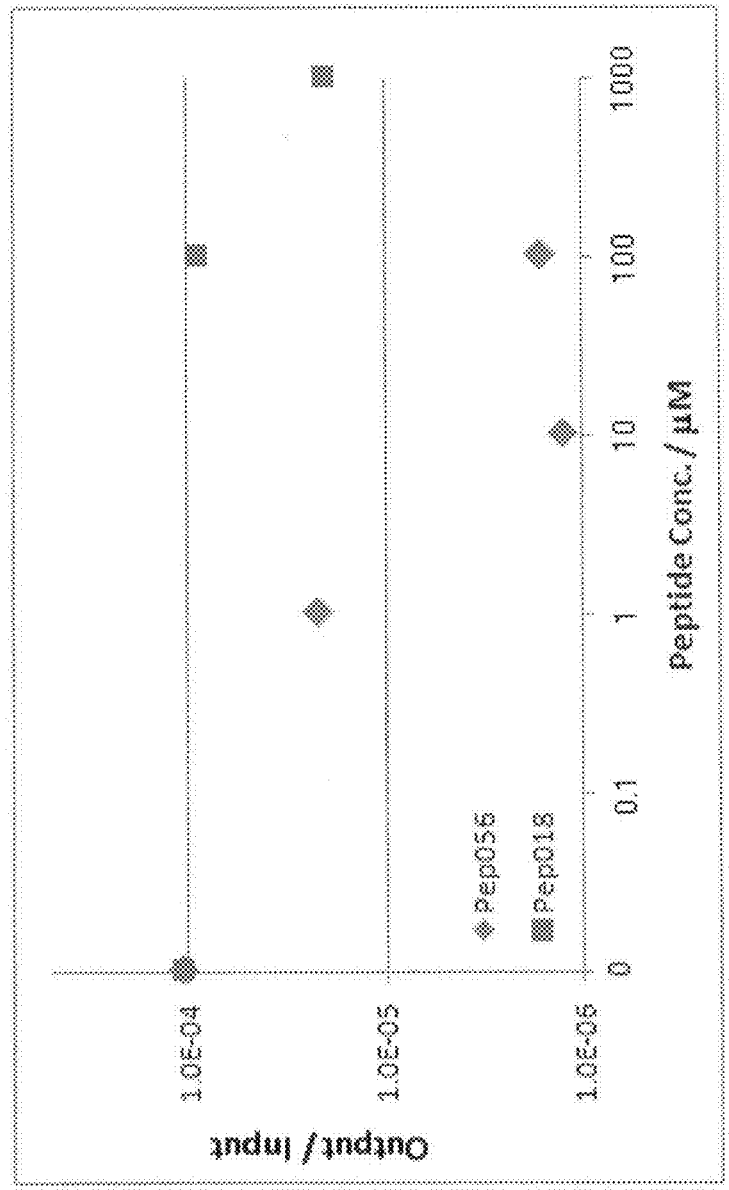
FIG. 7 shows a result of a competition test between an I-1012 phase and a peptide Pep056 or a peptide Pep018.
Figure 8:
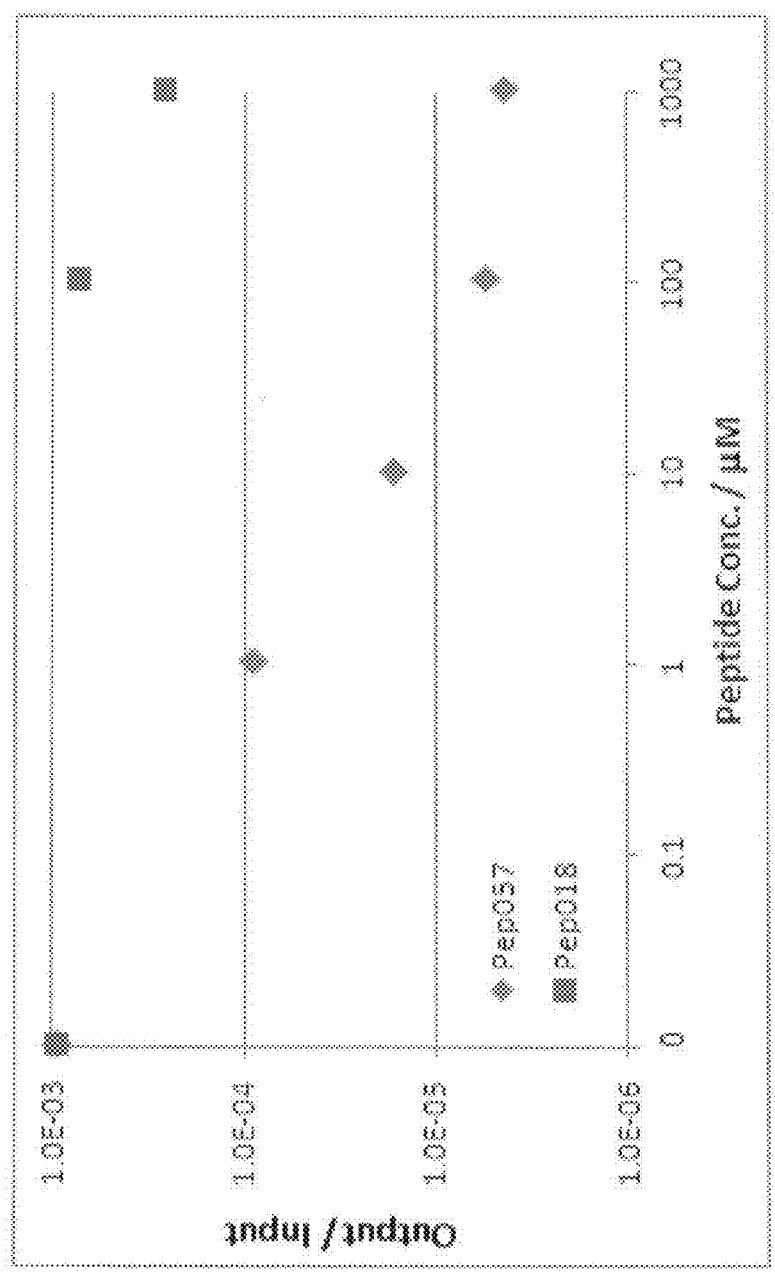
FIG. 8 shows a result of a competition test between an I-1015 phage and a peptide Pep057 or a peptide Pep018.

In the same manner, it was revealed from the results shown in FIGS. 7 and 8 that synthetic peptides Pep056 and Pep057, which have peptide sequences displayed by the I-1012 and I-1015 phages, inhibit binding of each of the phages to EGFR. Therefore, it can be considered that even though each of peptides displayed by the I-1012 and I-1015 phages is single, the peptide binds to the same site where the phage binds to EGFR.

Example 6 (Preparation of Alanine Substituted Phage)

[Procedure]
1. Site-Directed Mutagenesis

A phage obtained by substituting an amino acid in a peptide displayed site of an M13KE phage with alanine was prepared using a KOD-Plus-Mutagenesis kit (SMK-101, TOYOBO). An oligonucleotide primer having a nucleotide sequence of the displayed peptide sequence, which contains desired mutation, was entrusted with synthesis (NIHON GENE RESEARCH LABORATORIES Inc.). The synthesized primer was desalinated oligonucleotide that was purified by HPLC. The primer synthesized in this time had a length of 18 to 34 bp and was designed to have a GC content of 50 to 60%. In the KOD-Plus-Mutagenesis Kit used in this procedure, phosphorylation can be conducted at the same time as self ligation of a PCR product, and thus, phosphorylation of the primer was not carried out. Template plasmid DNA was purified from the I-1010, I-1012, and I-1015 phage infected ER2738 bacteria using a QIAGEN Plasmid kit (QIAGEN).

PCR was carried out in the condition of [94° C., 2 minutes]→{[98° C., 10 seconds]→[68° C., 7.5 minutes]}×8 cycles→[4° C., Hold] using the template plasmid DNA, the primer, dNTPs, and KOD-plus-. A thermal cycler (PCR Thermal Cycler Dice, TAKARA) was employed in the PCR reaction. The PCR reaction conditions were designed based on an amplification size.

Digestion of the template plasmid was conducted by a DpnI treatment, and self ligation of a PCR product was carried out by a T4 polynucleotide kinase treatment.
2. Genetic Transformation XL-1 Blue competent cells were dissolved on ice. 15 μL of a solution treated by self-ligation was added to 60 μL of the XL-1 Blue competent cells and mixed. The mixture was incubated on ice for 30 minutes, then incubated on a heated block at 42° C. for 90 seconds and incubated on ice for 2 minutes. 1 μL of the above described XL-Blue bacteria was added to 100 μL of an O/N culture of ER2738 bacteria in a 15 mL-conical tube and mixed. 74 μL of the XL-1 Blue bacteria were added in a 15 mL-conical tube. 4 mL of a top ager was added to each of the above described samples and mixed by a vortex mixer. The above described *Escherichia coli* sample was inoculated on an LB/IPTG/Xgal plate and inoculated at 37° C. for 16 hours.
3. Sequence Analysis of Variant Blue plaques obtained on the LB/IPTG/Xgal plate were cloned according to a general method (Phage Display A Laboratory Manual, Cole Spring Harbor Laboratory Press, 2001) and a basic sequence of a phage displayed peptide moiety was determined.
[Result]

For the I-1010 phage, alanine substituted phages having SEQ ID Nos. 11 to 21 shown in FIG. 9 were obtained.

In the same manner, for the I-1012 phage, alanine substituted phages having SEQ ID Nos. 22 to 33 shown in FIG. 10 were obtained, and for the I-1015 phage, alanine substituted phages having SEQ ID Nos. 34 to 45 shown in FIG. 11 were obtained.

Example 7 (Binding Property Test of Alanine Substituted Phage)

[Procedure]

A rhEGFR that is a target protein was added to a 96-well microplate to be 1 μg/well, and stood still at 4° C. overnight to be thus formed into a solid phase. A protein solution was removed, 300 μl of a blocking buffer was added and the mixture was incubated at 37° C. for 1 hour to thus block the wells. After removal of the blocking buffer, the wells were washed three times with 200 μl of 0.5% TBST washing solution, and finally 100 μl of 0.5% TBST was added thereto. An amplification phage solution (I-1010, I-1012 and I-1015 phages or the alanine substituted phage prepared in Example 6) was added to the above described wells to have 1×10¹⁰ PFU and mixed by pipetting. In the reaction, the mixture was gently shaken at room temperature for 1 hour. The reaction solution was removed and the wells were washed with 200 μl of 0.5% TBST ten times, 100 μl of 0.2 M glycine-HCl (pH 2.2) was then added to the wells and stirred by pipetting, thereafter gently shaking at room temperature for 10 minutes. The eluate was collected to a microtube from the wells and added with 15 μl of 1 M Tris-HCl (pH 9.1) to be neutralized and a target binding phage solution was thus obtained. The binding ability of the collected phage was examined by a measurement of a titer.
[Result]

Figure 12:
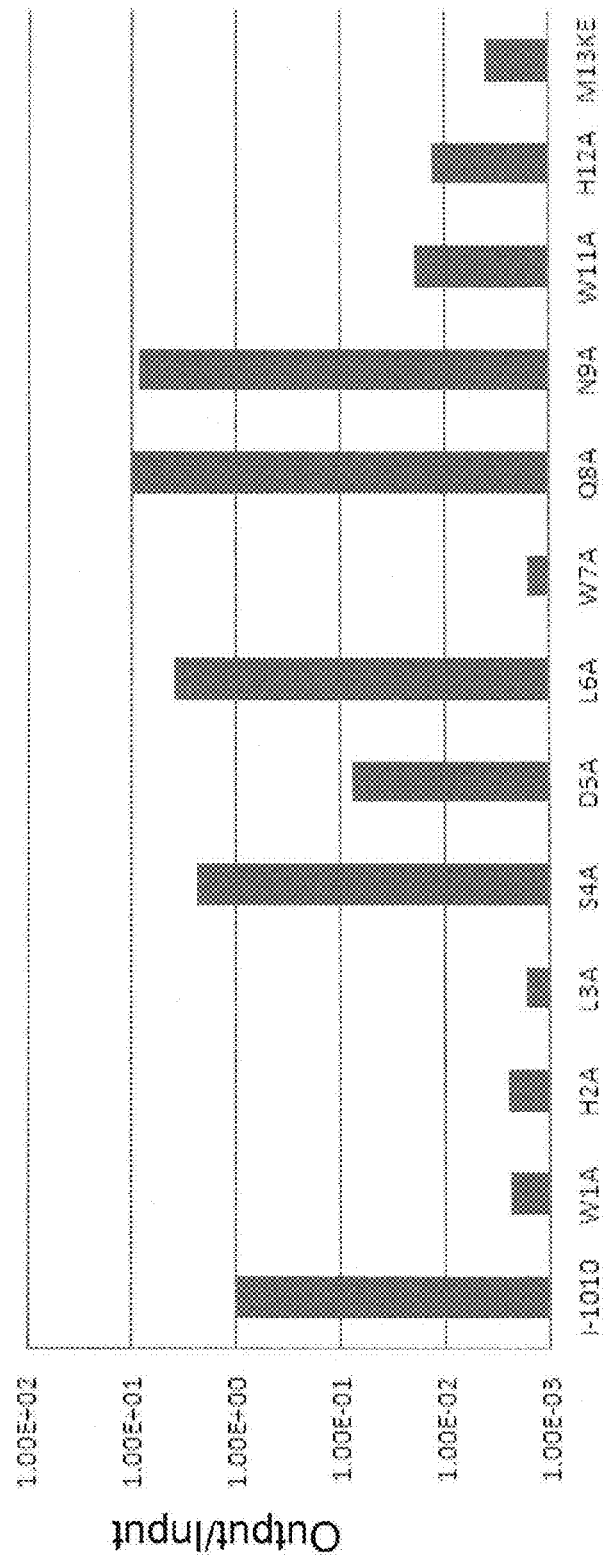
FIG. 12 shows a result of a binding property test of an I-1010 alanine substituted phage binding to a rhEGFR.
Figure 13:
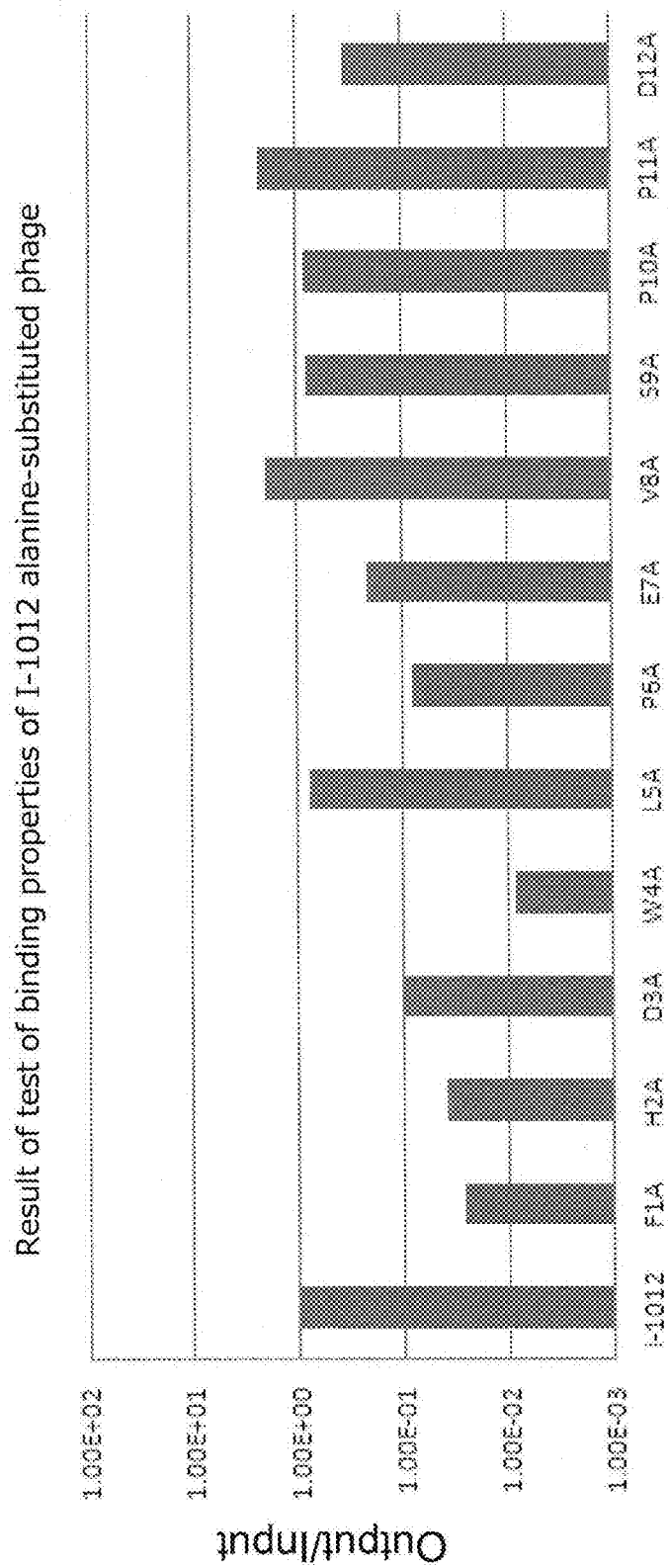
FIG. 13 shows a result of a binding property test of an I-1012 alanine substituted phage binding to a rhEGFR.
Figure 14:
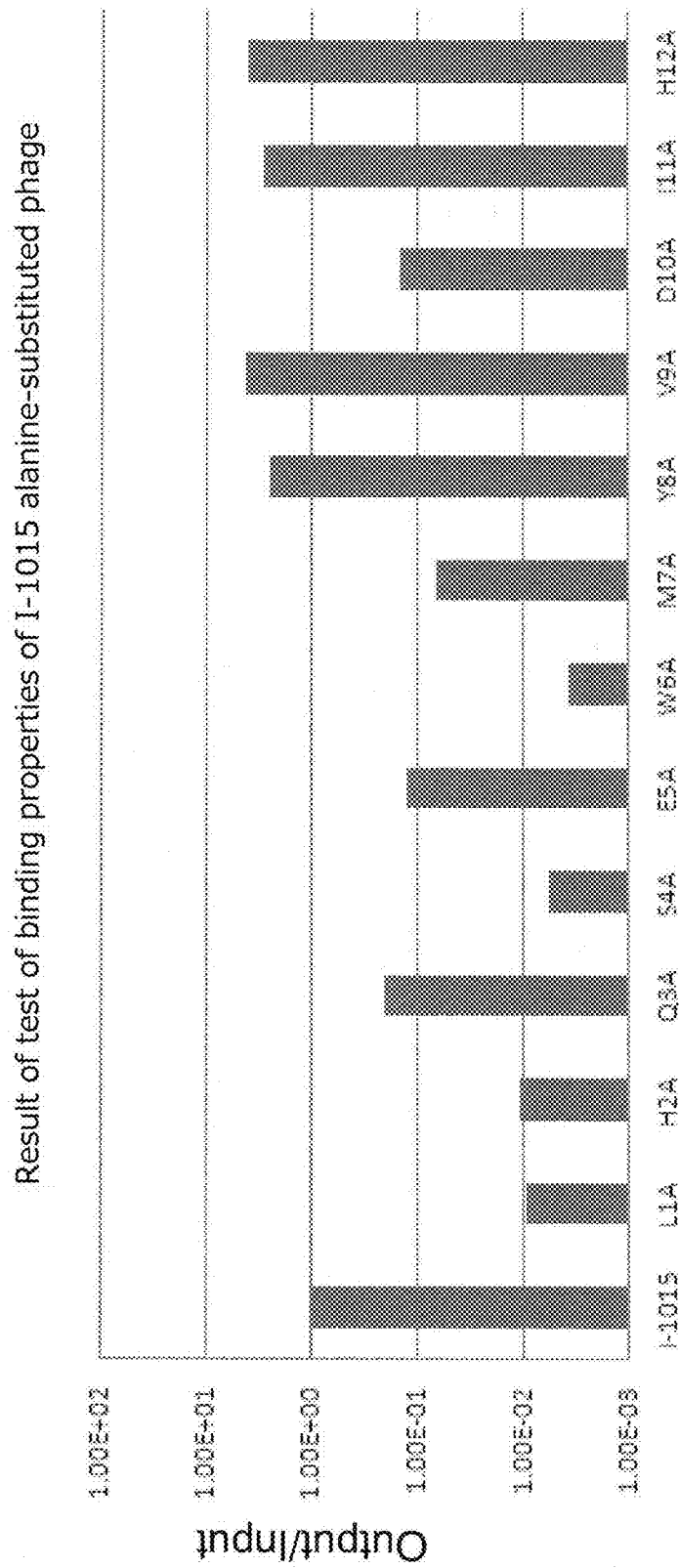
FIG. 14 shows a result of a binding property test of an I-1015 alanine substituted phage binding to a rhEGFR.

Changes in values of ratios of input titers/output titers in the binding property tests of alanine substituted phages are shown in FIG. 12 for the I-1010 phage, shown in FIG. 13 for the I-1012 phage, and shown in FIG. 14 for the I-1015 phage.

As found from FIG. 12, 7 kinds of phages having decreased binding properties as compared to the I-1010 phage existed and were phages in which the 1st, 7th and 11th W (Trp), the 2th and 12th H (His), the 3rd L (Leu), and the 5th D (Asp) were substituted with alanine (Ala).

In particular, binding properties of phages obtained by substituting the 1st and 7th W (Trp), the 2th H (His) and the 3rd L (Leu) in a peptide displayed by the I-1010 phage with alanine (Ala) were significantly reduced.

It was revealed from the above described result that amino acids which are assumed to contribute to binding of the I-1010 phage to EGFR were the 1st, 7nd and 11th W, the 2nd and 12nd H, the 3rd L and the 5th D.

Among these amino acids, amino acids that are considered to particularly contribute to binding to a rhEGFR were the 1st and 7th W, the 2nd H and the 3rd L.

Next, as found from FIG. 13, 5 kinds of phages having decreased binding properties as compared to the I-1012 phage existed and were phages in which the 1st F (Phe), the 2nd H (His), the 3rd D (Asp), the 4th W (Trp) and 6th P (Pro) were substituted with alanine (Ala). Therefore, it was revealed that amino acids which are considered to contribute to binding of the I-1012 phage to a rhEGFR were the 1st F, the 2nd H, the 3rd D, the 4th W and the 6th P.

Among these amino acids, amino acids that are considered to particularly contribute to binding to a rhEGFR were the 1st F, the 2nd H and the 4th W.

As found from FIG. 14, 5 kinds of phages having decreased binding properties as compared to the I-1015 phage existed and were phages in which the 1st L (Leu), the 2nd H (His), the 4th S (Ser), the 6th W (Trp) and the 7th M (Met) were substituted with alanine. In particular, binding properties of phages obtained by substituting the 4th S and the 6th W in a peptide displayed by the I-1015 phage with alanine were significantly reduced.

It was revealed from the above described result that amino acids which are assumed to contribute to binding of the I-1015 phage to a rhEGFR were the 1st L, the 2nd H, the 4th S, the 6th W and the 7th M.

Among these amino acids, amino acids that are considered to particularly contribute to binding to a rhEGFR were the 4th S and the 6th W.

Example 8 (Preparation of Amino Acid Substituted Phage)

[Procedure]
A mutant phage obtained by substituting an amino acid in a peptide displayed moiety of an M13KE phage with another amino acid was prepared in the same procedure as in Example 6. Hereinafter, a procedure of an operation of alanine scan is referred.
[Result]
I-1010 amino acid substituted phages (SEQ ID Nos. 46 to 53) displaying peptides shown in FIG. 15 were obtained.

Example 9 (Binding Property Test of Amino Acid Substituted Phage)

Figure 16:
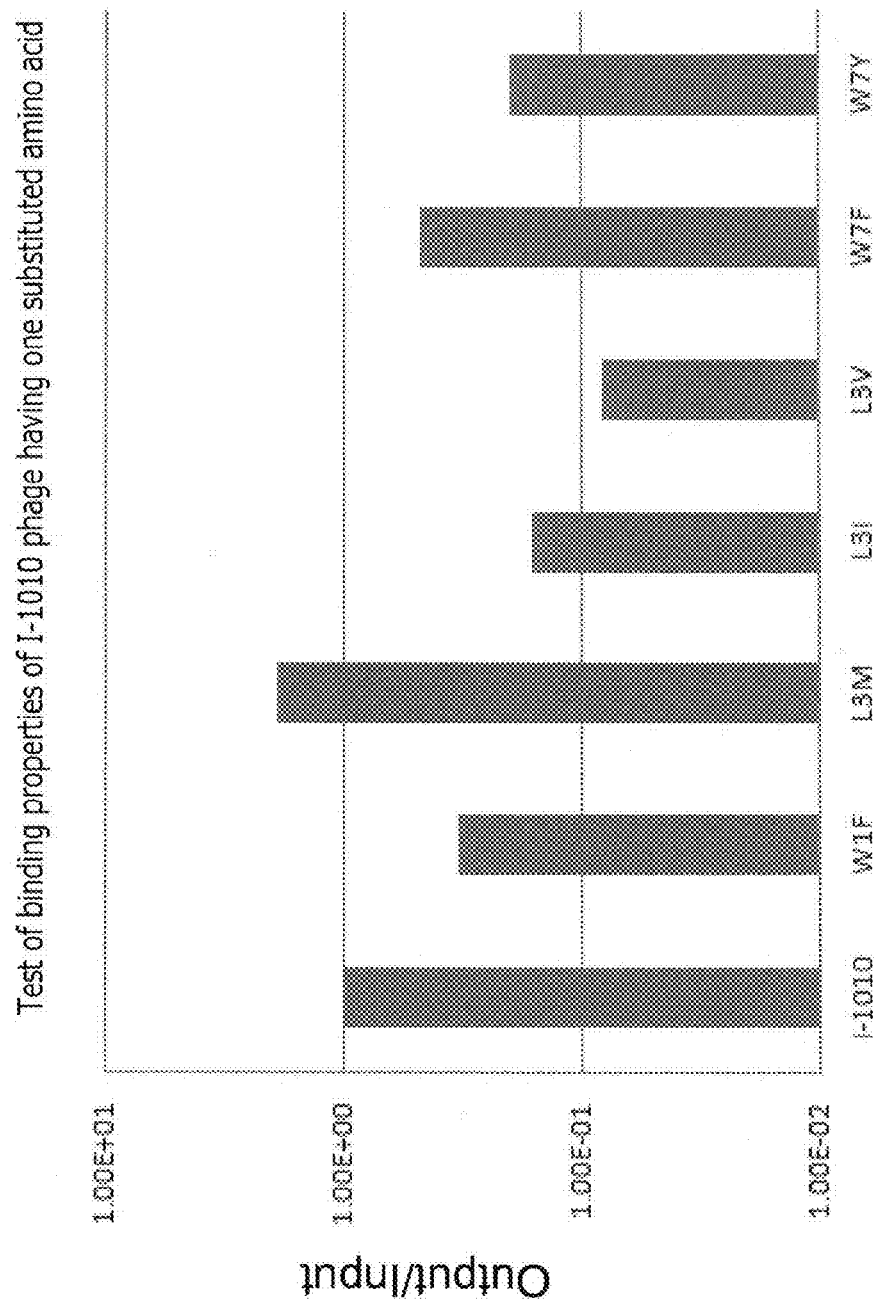
FIG. 16 shows a result of a binding property test of an I-1010 phage with one substituted amino acid binding to a rhEGFR.

[Procedure]
A rhEGFR that is a target protein was added to a 96-well microplate to be 1 μg/well, and stood still at 4° C. overnight to be thus formed into a solid phase. A protein solution was removed, 300 μl of a blocking buffer (5 mg/mL BSA/TBS) was added and the mixture was incubated at 37° C. for 1 hour to thus block the wells. After removal of the blocking buffer, the wells were washed with 200 μl of 0.5% TBST (0.5% Tween20/TBS) being the washing solution three times and thereto was finally added 100 μl of 0.5% TEST. An amplification phage solution was added to the above described wells to have $1 \times 10^{10}$ PFU and mixed by pipetting. In the reaction, the mixture was gently shaken at room temperature for 1 hour. The reaction solution was removed and the wells were washed with 200 μl of 0.5% TBST ten times, 100 μl of 0.2 M glycine-HCl (pH 2.2) was then added to the wells and stirred by pipetting, thereafter gently shaking at room temperature for 10 minutes. The eluate was collected to a microtube from the wells and added with 15 μl of 1 M Tris-HCl (pH 9.1) to be neutralized and a target binding phage solution was thus obtained. The binding ability of the collected phage was examined by a measurement of a titer.
[Result]
Result of Phage Having One Substituted Amino Acid
FIG. 16 shows changes in values of ratios of input titers to output titers in a binding property test of a phage having one substituted amino acid.

6 kinds of phages showing equivalent to about 1/10 binding properties as compared to the binding property of the I-1010 phage existed and are phases (SEQ ID Nos. 46 to 51) in which the 1st W was substituted with F, the 3rd L was substituted with M (Met), I (Ile) or V (Val), and the 7th W was substituted with F or Y (Tyr).
Result of Phage Having Two Substituted Amino Acids
Two sites were simultaneously substituted in an amino acid residue having lower change as compared to the binding property of the I-1010 phage from the binding property of the alanine substituted phage in FIG. 12 and the result of the binding property test of a phage having one substituted amino acid in FIG. 16.

Figure 17:
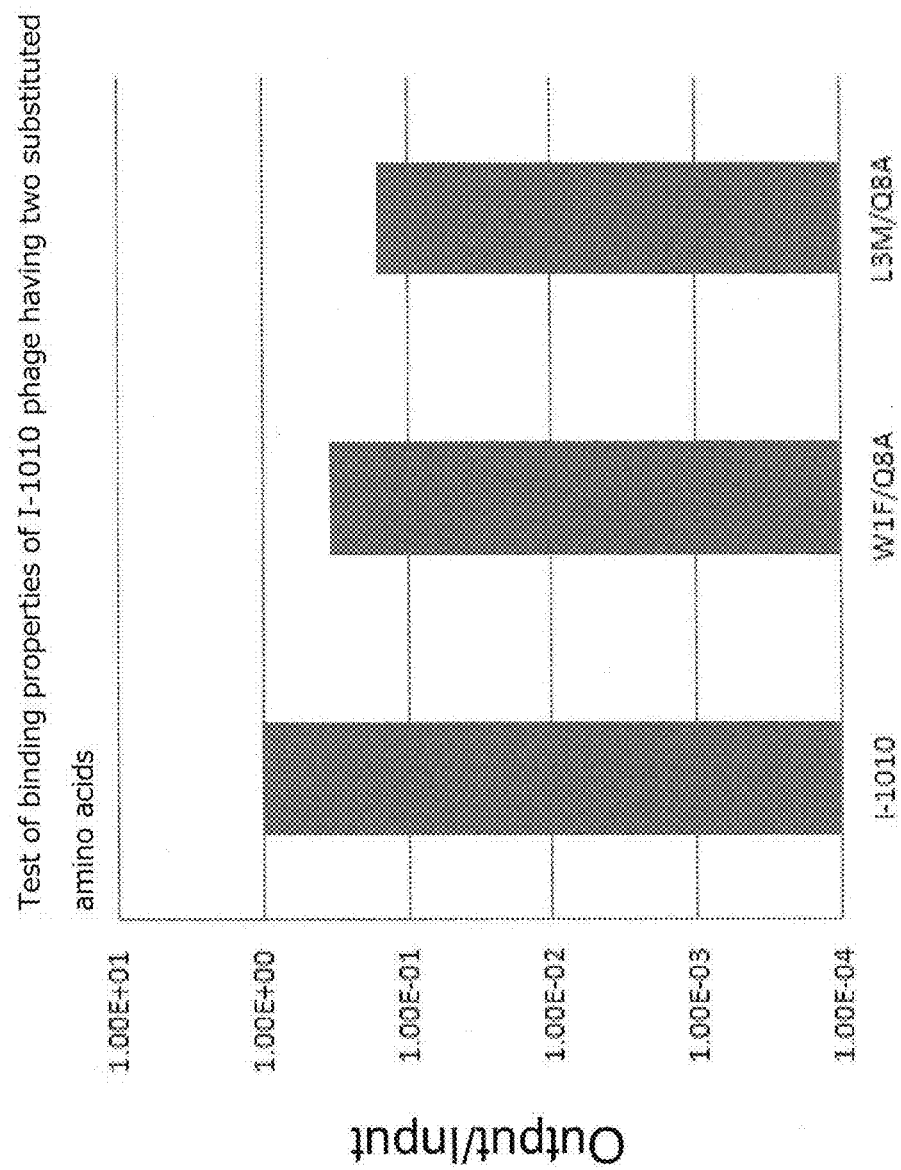
FIG. 17 shows a result of a binding property test of an I-1001 phage with two substituted amino acids binding to a rhEGFR.

FIG. 17 shows changes in values of ratios of input titers to output titers in the binding property test of a phage having two substituted amino acids.

Phages obtained by substituting two amino acids, which was carried out in this test, were a phage in which the 1st W was substituted with F and the 8th Q was substituted with A (W1F/Q8A, SEQ ID No. 52), a phage in which 3rd L was substituted with M and the 8th Q was substituted with A (L3M/Q8A, SEQ ID No. 53), and both phages resulted in showing equivalent to about 1/10 binding properties as compared to the binding property of the I-1010 phage.

Example 10 (Western Blotting)

EGFR expression amounts were evaluated by western blotting using human epidermal cancer derived A-431 cells (DS PHARMA BIOMEDICAL CO., LTD.) and human breast cancer derived MCF7 cells (DS PHARMA BIOMEDICAL CO., LTD.).

Figure 18:
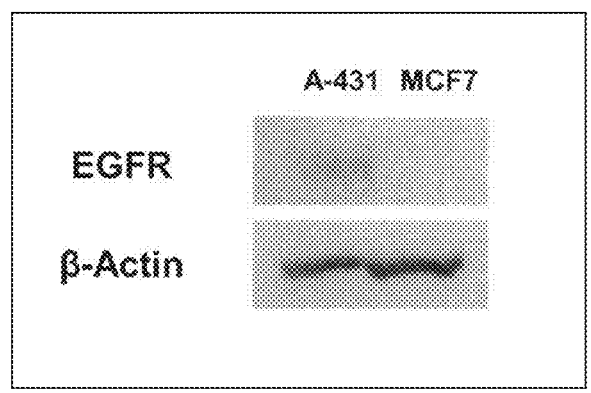
FIG. 18 shows EGFR expression amount (western blotting) of an A-431 cell and an MCF7 cell.

As a result, it was revealed that a result of evaluating EGFR expression amount of each cell by western blotting showed that EGFR was highly expressed in the A-431 cells (FIG. 18).

Example 11 (Binding Property Test (In Vitro))

Figure 19:
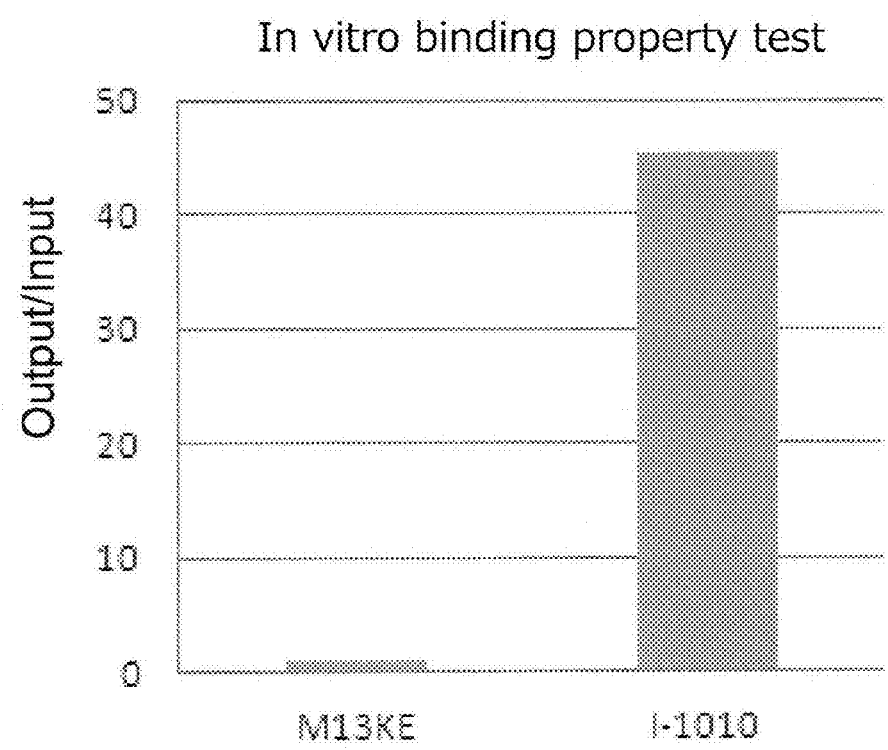
FIG. 19 shows a result of a binding property test of an I-1010 phage binding to an A-431 cell.

An A-431 cell line in which expression of EGFR protein was observed in Example 10 was used as the target and a binding property test of the I-1010 phage was carried out.
[Procedure]
A-431 cells were inoculated in a 6-well culture plate at $40 \times 10^4$ cells/well and cultured at 37° C. in the condition of 5% $CO_2$ overnight. The plate was incubated at 4° C. for 30 minutes and a medium in each well was removed, and treated by washing with 1 mL of 1% BSA/PBS twice. The I-1010 phage and the M13KE phage were diluted with 1 mL of a 10% FBS medium (growth medium) to have a titer of $1 \times 10^{10}$ PFU and added to each well, and incubated at 4° C. for 60 minutes. After the reaction, the reaction solution was removed and washed with 1 mL of 1% BSA/PBS ten times to remove non-binding phages. Thereto was added 100 μl of a 0.05% trypsin/0.53 mM EDTA solution and the reaction solution was incubated at 37° C. for about 10 minutes and added with 900 μl of a growth medium to prepare a collected phage solution. A titer of each collected phage solution was measured.
[Result]
FIG. 19 shows a ratio of an input titer to an output titer of each phage considering the number of collected cells. The titer ratio of the I-1010 phage was 45 times as high as that of the M13KE phage.

According to the above described result, the I-1010 phage showed binding properties not only to a genetically modified EGFR protein but also to EGFR expressed by cells.

Example 12 (In Vitro Imaging)

[Procedure]
A-431 cells were inoculated in a glass bottom dish to be $20 \times 10^4$ cells/dish and MCF7 cells were inoculated in a glass bottom dish to be $75 \times 10^4$ cells/dish, and cultured at 37° C. in the condition of $CO_2$ for 24 hours. After culturing each kind of the cells for a specified time, EGF was added to have a concentration of 100 ng/mL and the mixture was cultured for 6 days. Thereafter, the culture solution in the dish was removed and washed with 1000 μL of a growth medium at 37° C. ten times. An aminocaproic acid linker was connected to an N terminal of a peptide and the peptide in which FITC was labeled in the opposite side of the connected linker (Pep055-F, Pep032-F (YLPLWRLSESHM (peptide irrelevant to binding to EGFR): SEQ ID No. 54)) (purity 80.6%, HPLC grade, AnyGen, Korea) was prepared to be 100 μM in a growth medium, and 1 mL of the medium was added and incubated at 37° C. for 1 hour. A staining fluid was removed and washed with 1 mL of a growth medium at 37° C. three times and thereto was finally added 1 mL of the medium. For observation, fluorescent observation was carried out by irradiating an exciting light laser with a wavelength of 488 nm using a confocal microscope (Leica SP2).

[Result]

Figure 20:
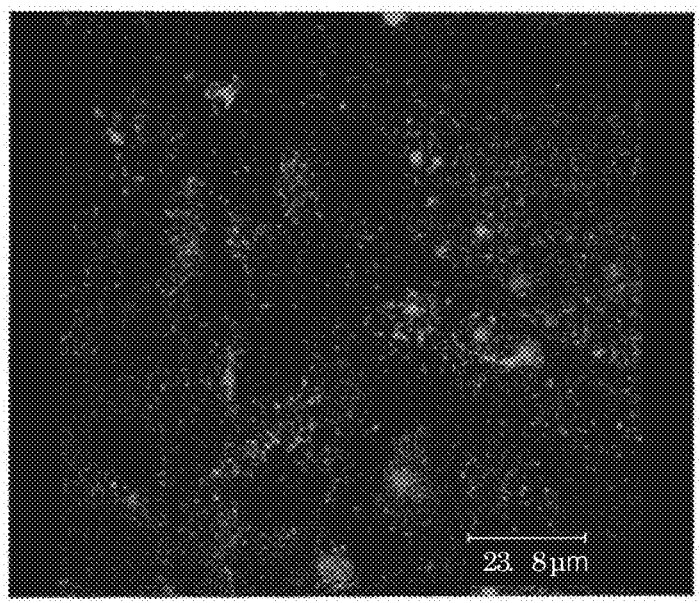
FIG. 20 shows stainability of an A-431 cell by Pep055-F.

FIG. 20 shows stainability of A-431 cells of Pep055-F observed by a confocal microscope. Staining of the cytoplasm of the A-431 cells was observed. The nucleus was not stained.

Figure 21:
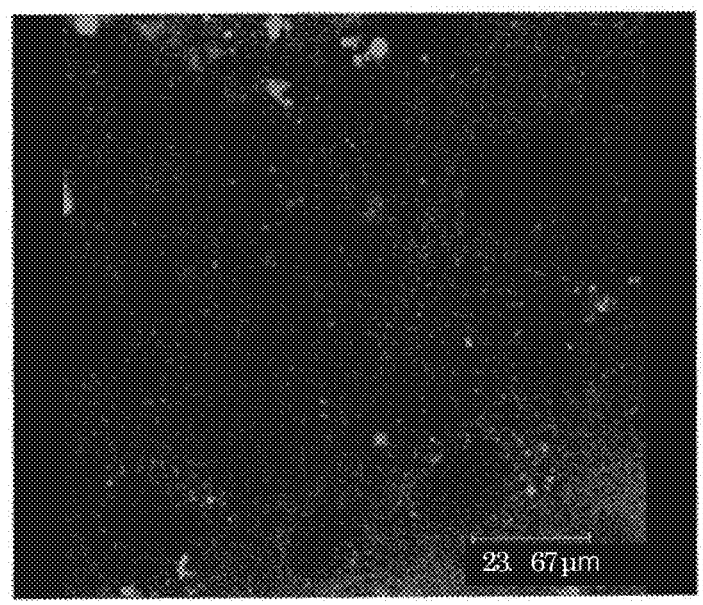
FIG. 21 shows stainability of an A-431 cell by Pep032-F.

FIG. 21 shows stainability of A-431 cells of Pep032-F observed by a confocal microscope. The control peptide scarcely stained the A-431 cells.

Figure 22:
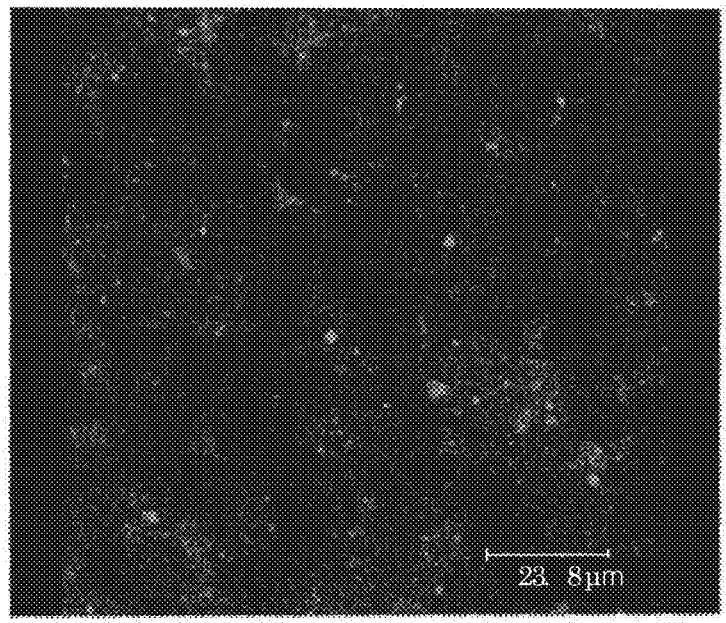
FIG. 22 shows stainability of an MCF7 cell by Pep055-F.
Figure 23:
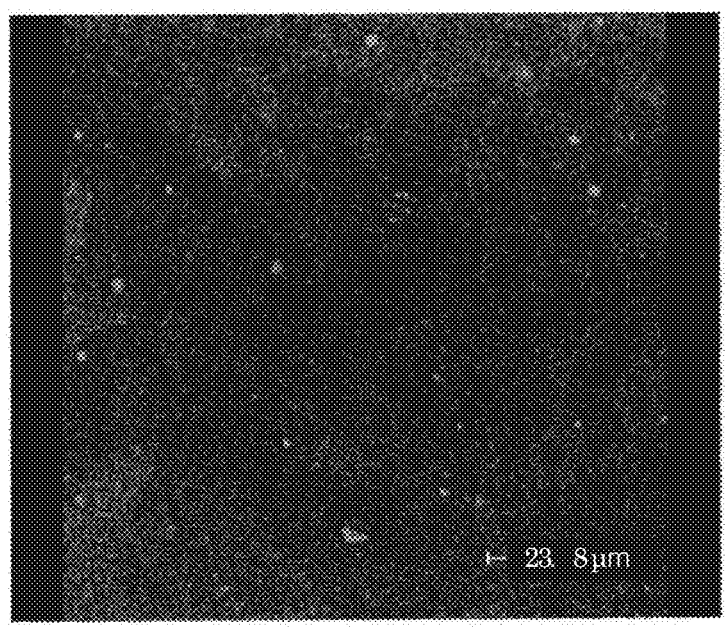
FIG. 23 shows stainability of an MCF7 cell by Pep032-F.

FIG. 22 shows stainability of MCF7 cells of Pep055-F observed by a confocal microscope, and FIG. 23 shows stainability of MCF7 cells of Pep032-F observed by a confocal microscope.

Both peptides scarcely stained the MCF7 cells.

According to the above described results, staining in a dot shape by Pep055-F, which was observed in the A-431 cells, was considered to be caused by EGFR expressed by the A-431 cells and also considered that Pep055-F binds to EGFR expressed by the cells.

Example 13 (Competition Test Between Recombinant Human EGF and I-1010 Phage)

[Procedure]

A rhEGFR that was a target protein was added to a 96-well microplate to be 1 μg/well, and stood still at 4° C. overnight to be thus formed into a solid phase. A protein solution was removed, 300 μl of a blocking buffer was added and the mixture was incubated at 37° C. for 1 hour to thus block the wells. After removal of the blocking buffer, the wells were washed with 200 μl of 0.5% TBST being the washing solution three times. 100 μl of a recombinant human EGF (rhEGF, Invitrogen) which is a ligand protein of EGFR diluted with 0.5% TBST to have each concentration was added and the mixture was gently shaken at room temperature for 1 hour. An I-1010 phage amplification phage solution was added to the above described wells to have $1\times10^{10}$ PFU and mixed by pipetting. In the reaction, the mixture was gently shaken at room temperature for 15 minutes. The reaction solution was removed and the wells were washed with 200 μl of 0.5% TBST ten times, and 100 μl of 0.2 M glycine-HCl (pH 2.2) was then added to the wells and stirred by pipetting, thereafter gently shaking at room temperature for 10 minutes. The eluate was collected to a microtube from the wells and added with 15 μl of 1 M Tris-HCl (pH 9.1) to be neutralized and a target binding phage solution was thus obtained. The binding ability of the collected phage was examined by a measurement of a titer.

[Result]

Figure 24:
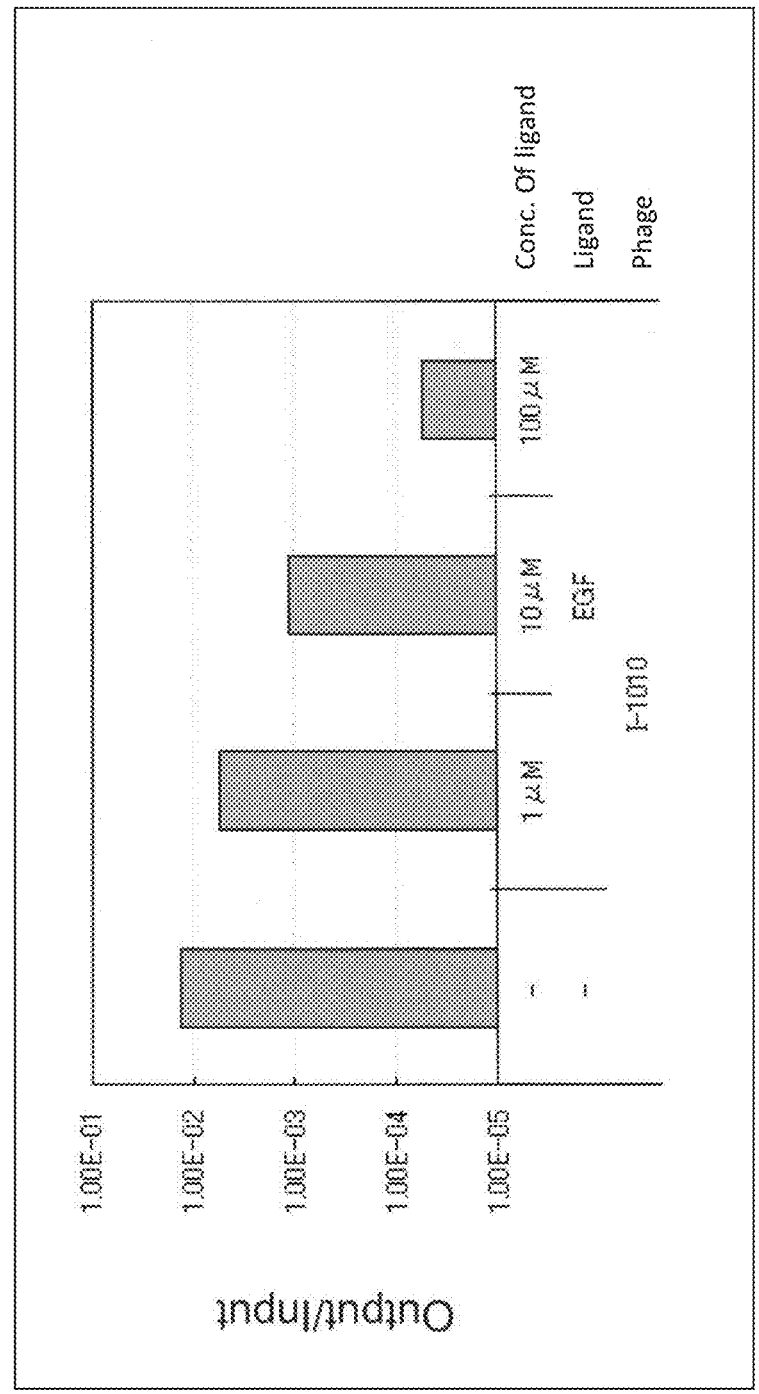
FIG. 24 shows a result of a competition test between a rhEGF and an I-1010 phage.

FIG. 24 shows changes in values of ratios of input titers/output titers in a competition test of a rhEGF and an I-1010 phage.

When a rhEGF was added, binding properties of an I-1010 phage to the rhEGFR decreased along with increasing the adding concentration.

According to the above described result, it was revealed that a rhEGF inhibits binding of an I-1010 phage to a rhEGFR from the fact that the binding properties of the I-1010 phage decrease concentration-depending to the adding concentration of the rhEGF. That is, an I-1010 phage is considered to be able to inhibit binding of EGF to EGFR and a peptide displayed by the I-1010 phage could be an inhibitor of EGF.

The invention claimed is:

1. A 12 to 18 amino acid peptide comprising the amino acid sequence represented by at least formula (1), (2), or (3):

$X^1$-His-$X^2$-$X^3$-Asp-$X^4$-$X^5$-$X^6$-$X^7$-$X^8$-Trp-His (1) (SEQ ID NO:55)

wherein $X^1$ is Trp or Phe;
$X^2$ is Leu, Met, or Ile;
$X^3$ is Ser, Ala, Thr, Gly, or Asn;
$X^4$ is Leu, Met, Ile, Val, or Ala;
$X^5$ is Trp, Phe, or Tyr;
$X^6$ is Gln, Asn, or Ala;
$X^7$ is Asn, Gln, or Ala; and
$X^8$ is Ala;

Phe-His-Asp-Trp-$X^{11}$-Pro-$X^{12}$-$X^{13}$-$X^{14}$-$X^{15}$-$X^{16}$-$X^{17}$ (2) (SEQ ID NO:56)

wherein $X^{11}$ is Leu or Ala;
$X^{12}$ is Glu or Ala;
$X^{13}$ is Val, Ala, Leu, or Ile;
$X^{14}$ is Ser or Ala;
$X^{15}$ is Pro or Ala;
$X^{16}$ is Pro, Val, Ile, or Ala; and
$X^{17}$ is Asp or Ala; and Leu-His-$X^{21}$-Ser-$X^{22}$-Trp-Met-$X^{23}$-$X^{24}$-$X^{25}$-$X^{26}$-$X^{27}$ (3) (SEQ ID NO:57)

wherein $X^{21}$ is Gln or Ala;
$X^{22}$ is Glu or Ala;
$X^{23}$ is Tyr, Phe, Trp, His, or Ala;
$X^{24}$ is Val, Ala, Leu, or Ile;
$X^{25}$ is Asp or Ala;
$X^{26}$ is Ile, Val, Leu, Met, or Ala; and
$X^{27}$ is His, Tyr, Phe, Lys, Arg, or Ala.

2. The peptide according to claim 1, wherein in the formula (1), $X^1$ is Trp or Phe, $X^2$ is Leu, Met, or Ile, $X^3$ is Ser or Ala, $X^4$ is Leu or Ala, $X^5$ is Trp, Phe, or Tyr, $X^6$ is Gln or Ala, $X^7$ is Asn or Ala, and $X^8$ is Ala.

3. The peptide according to claim 1, wherein, in formula (1), $X^1$ is Trp, $X^2$ is Leu or Met, $X^3$ is Ser or Ala, $X^4$ is Leu or Ala, $X^5$ is Trp, $X^6$ is Gln or Ala, $X^7$ is Asn or Ala, and $X^8$ is Ala.

4. The peptide according to claim 1, wherein, in formula (2), $X^{11}$ is Leu or Ala, $X^{12}$ is Glu or Ala, $X^{13}$ is Val or Ala, $X^{14}$ is Ser or Ala, $X^{15}$ is Pro or Ala, $X^{16}$ is Pro or Ala, and $X^{17}$ is Asp or Ala.

5. The peptide according to claim 1, wherein, in formula (2), $X^{11}$ is Leu, $X^{12}$ is Glu, $X^{13}$ is Val or Ala, $X^{14}$ is Ser, $X^{15}$ is Pro, $X^{16}$ is Pro or Ala, and $X^{17}$ is Asp.

6. The peptide according to claim 1, wherein, in formula (3), $X^{21}$ is Gln or Ala, $X^{22}$ is Glu or Ala, $X^{23}$ is Tyr or Ala, $X^{24}$ is Val or Ala, $X^{25}$ is Asp or Ala, $X^{26}$ is Ile or Ala, and $X^{27}$ is His or Ala.

7. The peptide according to claim 1, wherein, in formula (3), $X^{21}$ is Gln, $X^{22}$ is Glu, $X^{23}$ is Tyr or Ala, $X^{24}$ is Val or Ala, $X^{25}$ is Asp, $X^{26}$ is Ile or Ala, and $X^{27}$ is His or Ala.

8. The peptide according to claim 1, having epidermal growth factor receptor (EGFR) binding properties.

9. A pharmaceutical agent comprising the peptide according to claim 1 or a labeled product thereof.

10. A detection agent for a cancer cell or a cancer tissue comprising the peptide according to claim 1 or a labeled product thereof.

* * * * *

UNITED STATES PATENT AND TRADEMARK OFFICE
CERTIFICATE OF CORRECTION

PATENT NO. : 9,822,148 B2
APPLICATION NO. : 14/410329
DATED : November 21, 2017
INVENTOR(S) : Yusuke Iimori et al.

It is certified that error appears in the above-identified patent and that said Letters Patent is hereby corrected as shown below:

In the Claims

At Column 45, Line 40 (Claim 1, Line 10), please change "Gin," to --Gln,--.

At Column 45, Line 54 (Claim 1, Line 24), please change "Gin" to --Gln--.

At Column 45, Line 57 (Claim 1, Line 27), please change "Iie;" to --Ile;--.

Signed and Sealed this
Thirtieth Day of October, 2018

Andrei Iancu
*Director of the United States Patent and Trademark Office*